(12) United States Patent
Kido et al.

(10) Patent No.: US 8,597,799 B2
(45) Date of Patent: Dec. 3, 2013

(54) ORGANOSULFUR COMPOUND, PROCESS FOR PRODUCING THE SAME, AND ORGANIC ELECTROLUMINESCENCE ELEMENT USING THE SAME

(75) Inventors: Junji Kido, Yonezawa (JP); Tadashi Murakami, Tokyo (JP)

(73) Assignee: Ube Industries, Ltd., Ube-shi (JP)

( * ) Notice: Subject to any disclaimer, the term of this patent is extended or adjusted under 35 U.S.C. 154(b) by 254 days.

(21) Appl. No.: 13/058,504

(22) PCT Filed: Aug. 13, 2009

(86) PCT No.: PCT/JP2009/064300
§ 371 (c)(1),
(2), (4) Date: Feb. 10, 2011

(87) PCT Pub. No.: WO2010/018858
PCT Pub. Date: Feb. 18, 2010

(65) Prior Publication Data
US 2011/0140044 A1 Jun. 16, 2011

(30) Foreign Application Priority Data
Aug. 13, 2008 (JP) ................................. 2008-208789

(51) Int. Cl.
*H01L 51/54* (2006.01)
*C09K 11/06* (2006.01)
*C07C 315/04* (2006.01)
*C07C 317/14* (2006.01)
*C07D 401/14* (2006.01)

(52) U.S. Cl.
USPC ........... 428/690; 428/917; 313/504; 313/506; 568/34; 546/266

(58) Field of Classification Search
None
See application file for complete search history.

(56) References Cited

U.S. PATENT DOCUMENTS

| 3,953,519 | A | 4/1976 | Hay |
| 4,082,808 | A | 4/1978 | Hay |
| 2005/0065342 | A1 | 3/2005 | Shitagaki et al. |
| 2007/0077453 | A1 | 4/2007 | Sano et al. |

FOREIGN PATENT DOCUMENTS

| CN | 1775779 A | 5/2006 |
| CN | 101001901 A | 7/2007 |
| JP | 2002-008860 | 1/2002 |
| JP | A-2004-331588 | 11/2004 |
| JP | 2006-135160 | 5/2006 |
| JP | 2007-254297 | 10/2007 |
| JP | 2007-277221 | 10/2007 |
| SU | 820201 | 2/1982 |
| WO | WO 2005/009979 A1 | 2/2005 |
| WO | WO 2006/015862 A1 | 2/2006 |

OTHER PUBLICATIONS

Chemistry of Materials, (2012), vol. 24, pp. 1404-1406.*
Tetrahedron (2005), vol. 61, pp. 12314-12322.*
Office Action issued on Feb. 5, 2013 in Chinese Patent Application No. 200980140717.3.
Office Action issued in corresponding European Application No. 09806749.9 on Oct. 1, 2012.
Harvey, et al., "Synthesis and electronic spectra of substituted bis (hexaphenylbenzenes)," *Journal of Chemical and Engineering Data* (1977) 22:1, 110-113.
Ogliaruso, et al. "Bistetracyclones and bishexaphenylbenzenes, II ," *Journal of Organic Chemistry* (1965) 30:10 3354-3360.
International Search report issued in corresponding PCT Application No. PCT/JP2009/064300 mailed Sep. 15, 2009.
International Preliminary Report on Patentability and Written Opinion corresponding to PCT Application No. PCT/JP2009/064300, mailed Mar. 17, 2011.
Victory et al., "Crystal structure, spectroscopic study, molecular modeling, and in vitro antimicrobial activity testing of 2,2'-thiobis[4,6-diphenylpyridine-3-carbonitrile]" Journal of Chemical Crystallography, 24(10), 1994, 675-9.
Nishimura, et al., : Synthesis and antibacterial activity of 6-substituted-2-(3, 5-dimethyl-1-pyrazolyl)-4-phenyl- and-4-methylpyrimidines, Bokin Bobai , 7(4), 1979, T159-T171.
Loughran et al., "S-Triazines, I. Linear, sulfur bridged-s-triazine oligomers" Journal of Heterocyclic Chemistry, 3(2), 1966, 137-42.
Supplemental European Search Report issued in corresponding EP Application No. 09806749.9, mailed Sep. 30, 2011.

Office Action issued on Aug. 9, 2013 in Chinese Patent Application No. 200980140717.3.

Padmavathi et al., "A New Class of Sulfur-Linked Bis-1,2,3-selenadiazoles, 1,2,3-Thiadiazoles, and 2H-diazaphospholes", Heteroetom Chemistry, vol. 19, No. 3, 2008, pp. 261-265.

Purushothaman et al., "Synthesis of 4,5-diarylimidazoline-2-thiones and their photoconversion to bis(4,5-diarylimidazol-2-yl) sulphines", Indian Journal of Chemistry, vol. 29B(1), Jan. 1990, pp. 18-21.

Office Action issued on Oct. 15, 2013 in Japanese Patent Application No. 2010-524752.

\* cited by examiner

*Primary Examiner* — Dawn L. Garrett

(74) *Attorney, Agent, or Firm* — Knobbe Martens Olson & Bear LLP

(57) ABSTRACT

Disclosed is an organosulfur compound denoted by a general formula (a1):

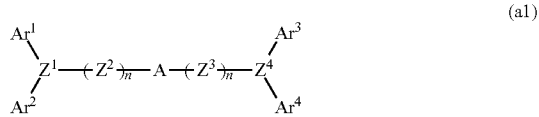

(a1)

in which A denotes —S—, —S(O)— or —S(O)$_2$—; $Z^1$ and $Z^4$ denote a trivalent aromatic hydrocarbon group or the like; $Z^2$ and $Z^3$ denote a bivalent aromatic hydrocarbon group or the like; $Ar^1$, $Ar^2$, $Ar^3$ and $Ar^4$ denote an aromatic hydrocarbon group or the like; and n is 0 or 1, or a general formula (b1):

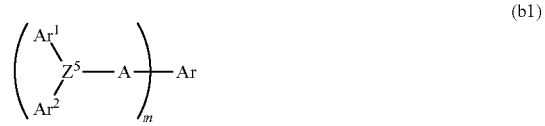

(b1)

in which A denotes the same meaning as aforesaid; $Z^5$ denotes a trivalent aromatic hydrocarbon group or the like; Ar denotes a m-valent aromatic hydrocarbon group or the like; $Ar^1$ and $Ar^2$ denote the aforesaid meaning; and m is 2 or 3. This compound is useful as an electron transport material, a hole blocking material or a host material of an organic electroluminescence element.

8 Claims, 1 Drawing Sheet

ORGANOSULFUR COMPOUND, PROCESS FOR PRODUCING THE SAME, AND ORGANIC ELECTROLUMINESCENCE ELEMENT USING THE SAME

This application is the U.S. National Phase under 35 U.S.C. §371 of International Application No. PCT/JP2009/064300, filed Aug. 13, 2009, designating the U.S., and published in Japanese as WO2010/018858 on Feb. 18, 2010, which claims priority to Japanese Patent Application No. 2008-208789, filed Aug. 13, 2008, the entire contents of which are incorporated herein by reference.

TECHNICAL FIELD

The present invention relates to an organosulfur compound useful as, for example, an electron transport material, a hole blocking material and a host material of an organic electroluminescence element, which may be occasionally abbreviated to as an organic EL element hereafter, and to a process of production thereof.

BACKGROUND ART

Various materials are proposed as the electron transport material and hole blocking material of an organic EL element. Organosulfur compounds are exemplified in the literature regarding compounds characterized in other chemical structural moieties, the Patent Document 1 (benzoisoindole-based compound), the Patent Documents 2 and 3 (carbazole-based compound), and the Patent Document 4 (compound with a pentaphenyl-substituted phenyl group backbone). In these literature, however, there is neither description of details of the organosulfur compounds exemplified nor the description of the specific examples that they are applied to elements.

Previously, no compound with the compound structures according to the present invention has been known, and its application as an organic EL material has not been considered at all.

LIST OF REFERENCES

Patent Document 1: Japanese Laid-open Patent Publication No. 2007-277221
Patent Document 2: Japanese Laid-open Patent Publication No. 2002-8860
Patent Document 3: Japanese Laid-open Patent Publication No. 2007-254297
Patent Document 4: Japanese Laid-open Patent Publication No. 2006-135160

SUMMARY OF INVENTION

Problems to be Solved by the Invention

The problem of the present invention is to solve the problems mentioned above, and to provide an organosulfur compound useful as an electron transport material and hole blocking material, and host material of an organic electroluminescence element by means of a simple process.

Means for Solving the Problems

The present invention relates to an organosulfur compound denoted by a general formula (a1):

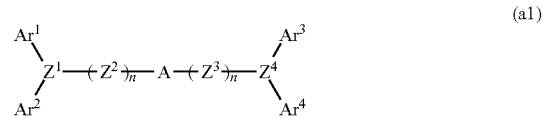

(a1)

in which,
A denotes —S—, —S(O)— or —S(O)$_2$—,
$Z^1$ and $Z^4$ independently of one another denote a trivalent aromatic hydrocarbon group or aromatic heterocyclic group except carbazolyl group, which may have a substituent,
$Z^2$ and $Z^3$ independently of one another denote a bivalent aromatic hydrocarbon group or aromatic heterocyclic group, which may have a substituent,
$Ar^1$, $Ar^2$, $Ar^3$ and $Ar^4$ independently of one another denote an aromatic hydrocarbon group or an aromatic heterocyclic group except carbazolyl group, which may have a substituent, and
n is 0 or 1, and two of n may be the same or different,
or,
a general formula (b1):

(b1)

in which,
A denotes —S—, —S(O)— or —S(O)$_2$—,
$Z^5$ denotes a trivalent aromatic hydrocarbon group or aromatic heterocyclic group, which may have a substituent,
Ar denotes a m-valent aromatic hydrocarbon group or aromatic heterocyclic group, which may have a substituent,
$Ar^1$ and $Ar^2$ independently of one another denote the meaning defined for said general formula (a1),
m is 2 or 3,
wherein A, $Z^5$, $Ar^1$, and $Ar^2$ that are present in the formula with m occurrences may be, in each occurrence, the same or different one another.

Effect of the Invention

The organosulfur compound of the present invention can be preferably used as an electron transport material, hole blocking material, host material in an organic EL element.

DESCRIPTION OF EMBODIMENTS

Figure 1:
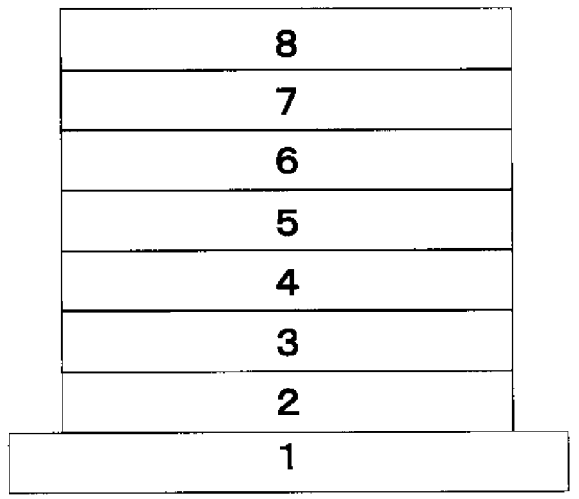
FIG. 1 shows the layer constitution of the organic EL element produced in the element production examples 1 to 4.

The organosulfur compound of the present invention is explained in two groups, that is separated into the compounds belonging to the aforesaid general formula (a1) and the compounds belonging to the aforesaid general formula (b1).

In the present application, monovalent, divalent and trivalent "aromatic hydrocarbon groups" mean the residues in which the valence number of H(s) is/are removed from an aromatic hydrocarbon compound. In the same way, monovalent, divalent and trivalent "aromatic heterocyclic groups" mean the residues in which the valence number of H(s) is/are removed from an aromatic heterocyclic compound.

The general formula (a1) is as follows.

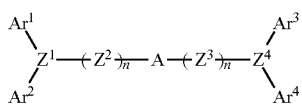
(a1)

In the general formula (a1), each parameter denotes the following meanings. In the general formula (a1), A denotes a thioether group, a sulfinyl group or a sulfonyl group, namely one of any groups among the formulae below.

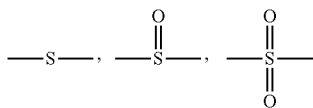

$Z^1$ and $Z^4$ are a trivalent aromatic hydrocarbon group or aromatic heterocyclic group except carbazolyl group, which may have a substituent. An aromatic hydrocarbon compound from which a trivalent aromatic hydrocarbon group is derived may be any of a monocyclic compound having one benzene ring and its derivative, a polycyclic compound such as biphenyl and terphenyl in which two or more benzene rings are bonded through a single bond, and a condensed polycyclic compound such as naphthalene, anthracene and phenanthrene in which two or more benzene rings are condensed to be bonded. An aromatic heterocyclic compound from which a aromatic heterocyclic group is derived includes, for example, a 6-membered ring compound such as pyridine, pyrimidine and pyridazine, and a 5-membered ring compound such as pyrazole, thiophene, pyrrole and oxazole.

$Z^1$ and $Z^4$ are preferably a residue derived from a monocyclic compound, including a residue derived from, for example, benzene, pyridine, pyrimidine, triazine, imidazole. These residues may be substituted with an alkyl group which preferably has 6 or less carbon atoms, a cycloalkyl group which is preferably a group having a 3- to 6-membered ring, an alkoxy group which preferably has 6 or less carbon atoms, or a halogen which is preferably fluorine.

$Z^1$ and $Z^4$ are preferably the following group.

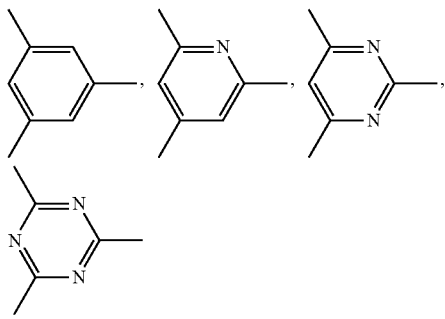

While $Z^1$ and $Z^4$ may be different, they are preferably the same.

In one preferred aspect of the present invention, $Z^1$ and $Z^4$ are denoted by the following group.

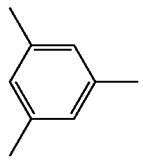

$Z^2$ and $Z^3$ are a divalent aromatic hydrocarbon group or aromatic heterocyclic group, which may have a substituent. An aromatic hydrocarbon compound which derives a divalent aromatic hydrocarbon group may be any of a monocyclic compound having one benzene ring and its derivative, a polycyclic compound such as biphenyl and terphenyl in which two or more benzene rings are bonded through a single bond, and a condensed polycyclic compound such as naphthalene, anthracene and phenanthrene in which two or more benzene rings are condensed to be bonded. An aromatic heterocyclic compound which derives an aromatic heterocyclic group includes, for example, a 6-membered ring compound such as pyridine, pyrimidine and pyridazine, and a 5-membered ring compound such as pyrazole, thiophene, pyrrole and oxazole.

$Z^2$ and $Z^3$ are preferably a residue derived from a monocyclic compound, including a residue derived from, for example, benzene, pyridine, pyridazine. These residues may be substituted with an alkyl group which preferably has 6 or less carbon atoms, a cycloalkyl group which is preferably a group having a 3- to 6-membered ring, an alkoxy group which preferably has 6 or less carbon atoms, or a halogen which is preferably fluorine.

$Z^2$ and $Z^3$ are preferably the following group.

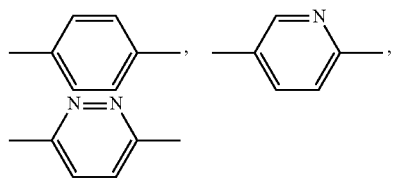

In one preferred aspect of the present invention, $Z^2$ and $Z^3$ are denoted by the following group.

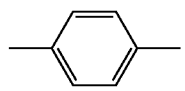

n denotes the number of $Z^2$ and $Z^3$, and it is 0 or 1. When n is 0, it means that $Z^1$ and/or $Z^4$ is directly bonded to A. While two of n may be the same or different, they are preferably the same.

$Ar^1$, $Ar^2$, $Ar^3$ and $Ar^4$ may be the same or different, and denote a monovalent aromatic hydrocarbon group or aromatic heterocyclic group except carbazolyl group, which may have a substituent. A monovalent aromatic hydrocarbon group (i.e. an aryl group) includes, for example, phenyl group, tolyl group, fluorophenyl group, xylyl group, biphenylyl group, naphthyl group, anthryl group, phenanthryl group and the like. A monovalent aromatic heterocyclic group, (i.e. a heteroaryl group) includes, for example, a heteroaryl group having a 6-membered ring structure such as pyridyl group, pyrimidyl group and pyridazyl group, a heteroaryl group having a 5-membered ring structure such as pyrazolyl group, thienyl group, pyrrole group and oxazolyl group. In one preferred aspect of the present invention, it is preferably phenyl group, pyridyl group.

While $Ar^1$, $Ar^2$, $Ar^3$ and $Ar^4$ may be the same or different, they all are preferably the same.

The aforesaid $Ar^1$, $Ar^2$, $Ar^3$ and $Ar^4$ may have a substituent, and the substituent includes a substituent capable of bonding through carbon atom, a substituent capable of bonding through oxygen atom, a substituent capable of bonding through nitrogen atom, a substituent capable of bonding through sulfur atom, a halogen atom and the like.

The aforesaid substituent capable of bonding through carbon atom includes, for example, an alkyl group such as methyl group, ethyl group, propyl group, butyl group, pentyl group, hexyl group; a cycloalkyl group such as cyclopropyl group, cyclobutyl group, cyclopentyl group, cyclohexyl group, cycloheptyl group; an alkenyl group such as vinyl group, allyl group, propenyl group, cyclopropenyl group, cyclobutenyl group, cyclopentenyl group; a heterocyclic group such as quinolyl group, pyridyl group, pyrrolidyl group, pyrrolyl group, furyl group, thienyl group; an aryl group such as phenyl group, tolyl group, fluorophenyl group, xylyl group, biphenylyl group, naphthyl group, anthryl group, phenanthryl group; an acyl group such as acetyl group, propionyl group, acryloyl group, pivaloyl group, cyclohexylcarbonyl group, benzoyl group, naphthoyl group, toluoyl group (the acyl group may be acetalized); carboxyl group; an alkoxycarbonyl group such as methoxycarbonyl group, ethoxycarbonyl group; an aryloxycarbonyl group such as phenoxycarbonyl group; an alkyl halide group such as trifluoromethyl group; cyano group. These groups include various isomers.

The aforesaid substituent capable of bonding through oxygen atom includes, for example, hydroxyl group; an alkoxyl group such as methoxyl group, ethoxyl group, propoxyl group, butoxyl group, pentyloxyl group, hexyloxyl group, heptyloxyl group, benzyloxyl group; an aryloxyl group such as phenoxyl group, tolyloxyl group, naphthyloxyl group. These groups include various isomers.

The aforesaid substituent capable of bonding through nitrogen atom includes, for example, a primary amino group such as methylamino group, ethylamino group, propylamino group, butylamino group, cyclohexylamino group, phenylamino group, naphthylamino group; a secondary amino group such as dimethylamino group, diethylamino group, dipropylamino group, dibutylamino group, methylethylamino group, methylpropylamino group, methylbutylamino group, diphenylamino group, N-methyl-N-methanesulfonylamino group; a heterocyclic amino group such as morpholino group, piperidino group, piperazinyl group, pyrazolidinyl group, pyrrolidino group, indolyl group; imino group. These groups include various isomers.

The aforesaid substituent capable of bonding through sulfur atom includes, for example, mercapto group; a thioalkyl group such as thiomethyl group, thioethyl group, thiopropyl; a thioaryl group such as thiophenyl group, thiotoluyl group, thionaphthyl group. These groups include various isomers.

The aforesaid halogen atom includes fluorine atom, chlorine atom, bromine atom, iodine atom.

The number and position of the aforesaid substituents are not particularly limited.

One of preferred compound groups among the organosulfur compounds of the general formula (a1) is the formula (a1) wherein $Z^2$ and $Z^3$ denote phenylene group which may have a substituent, and $Z^1$ and $Z^4$ are a trivalent residue derived from benzene, which may have a substituent. These compounds are denoted by the general formula (a2).

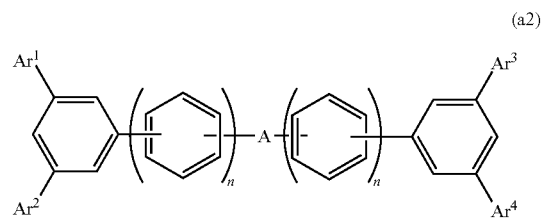

(a2)

$Z^2$ and $Z^3$ are more preferably 1,4-phenylene which may have a substituent, and these compounds are denoted by the general formula (a3).

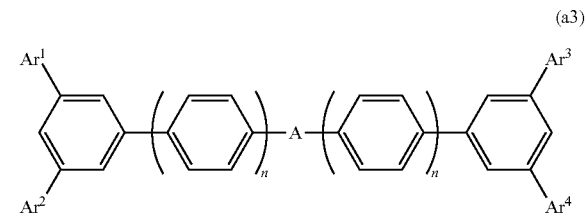

(a3)

Particular preference is given to the compounds wherein A denotes —S(O)$_2$—, which is denoted by the general formula (a4).

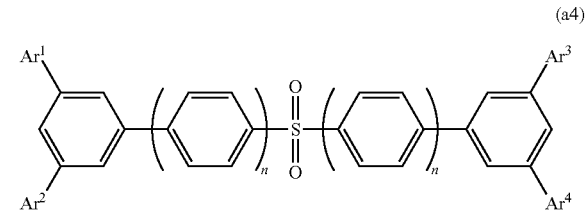

(a4)

In the formulae (a2), (a3) and (a4), $Ar^1$, $Ar^2$, $Ar^3$, $Ar^4$ and n are defined as beforehand. Any hydrogen atom on a benzene ring may also be substituted with an alkyl group which preferably has 6 or less carbon atoms, a cycloalkyl group which is preferably a group having a 3- to 6-membered ring, an alkoxy group which preferably has 6 or less carbon atoms, a halogen which is preferably fluorine.

The specific example of the organosulfur compound includes, for example, the compounds of the formulae (a5) and (a6).

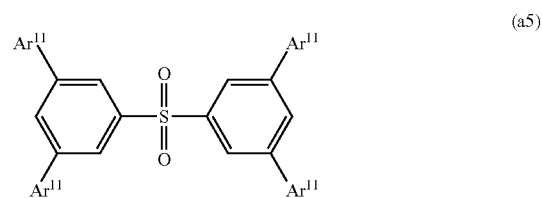

(a5)

-continued

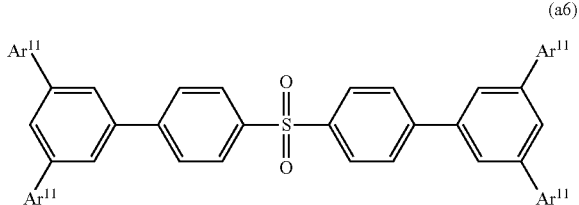
(a6)

in which, $Ar^{11}$ denotes phenyl group, tolyl group or pyridyl group.

Next, the compounds belonging to the general formula (b1) are explained. The general formula (b1) is as follows.

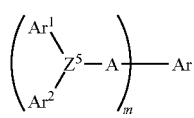
(b1)

In the general formula (b1), each parameter denotes the following meanings.

A denotes the meaning defined for the formula (a1).

$Z^5$ denotes a trivalent aromatic hydrocarbon group or aromatic heterocyclic group, which may have a substituent, and it includes the aromatic hydrocarbon group or aromatic heterocyclic group explained for $Z^1$ of the formula (a1), preferred groups of which are also the same.

$Ar^1$ and $Ar^2$ independently of one another denote the aromatic hydrocarbon group or aromatic heterocyclic group explained for $Ar^1$ and $Ar^2$ of the formula (a1), preferred groups of which are also the same.

m is 2 or 3.

Ar denotes a m-valent, namely divalent or trivalent aromatic hydrocarbon group or aromatic heterocyclic group. When Ar denotes a divalent group, it denotes the aromatic hydrocarbon group or aromatic heterocyclic group explained for $Z^2$ of the formula (a1), and preferably the preferred group denoted for $Z^2$.

When Ar denotes a trivalent group, it is a trivalent aromatic hydrocarbon group or aromatic heterocyclic group, which may have a substituent. An aromatic hydrocarbon compound from which a trivalent aromatic hydrocarbon group is derived may be any of a monocyclic compound having one benzene ring and its derivative, a polycyclic compound such as biphenyl and terphenyl in which two or more benzene rings are bonded through a single bond, and a condensed polycyclic compound such as naphthalene, anthracene and phenanthrene in which two or more benzene rings are condensed to be bonded. An aromatic heterocyclic compound from which a aromatic heterocyclic group is derived includes, for example, a 6-membered ring compound such as pyridine, pyrimidine and pyridazine, and a 5-membered ring compound such as pyrazole, thiophene, pyrrole and oxazole.

It is preferably a residue derived from a monocyclic compound, and it includes a residue derived from, for example, benzene, pyridine, pyrimidine, triazine, imidazole. These residues may be substituted with an alkyl group which preferably has 6 or less carbon atoms, a cycloalkyl group which is preferably a group having a 3- to 6-membered ring, an alkoxy group which preferably has 6 or less carbon atoms, a halogen which is preferably fluorine.

In a preferred embodiment of the present invention, Ar is preferably denoted by the following formulae.

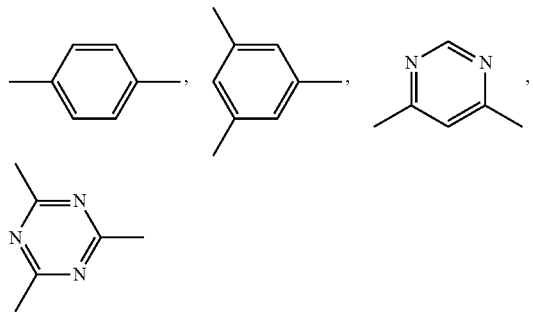

One of preferred compound groups among the organosulfur compounds of the general formula (b1) is the formula (b1) wherein $Z^5$ is a trivalent residue derived from benzene, which may have a substituent, and Ar is a divalent or trivalent residue derived from benzene, which may have a substituent. These compounds are denoted by the general formula (b2).

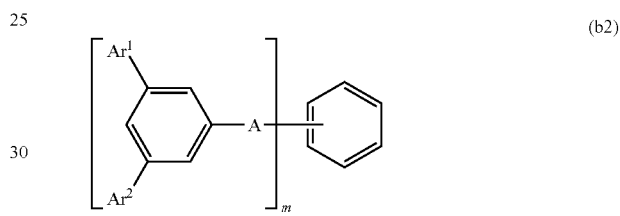
(b2)

The example of more specific structures of this compound includes the structure denoted by the following formula (b3) or (b4). Preference is also given to the structure wherein two of A are in a meta-position for the central benzene ring in the formula (b3).

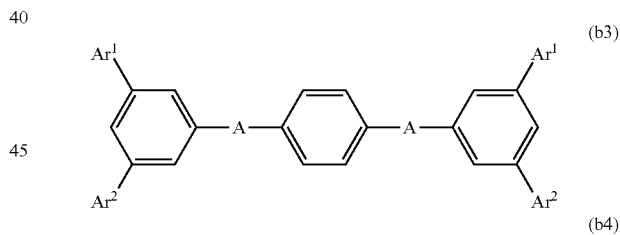
(b3)

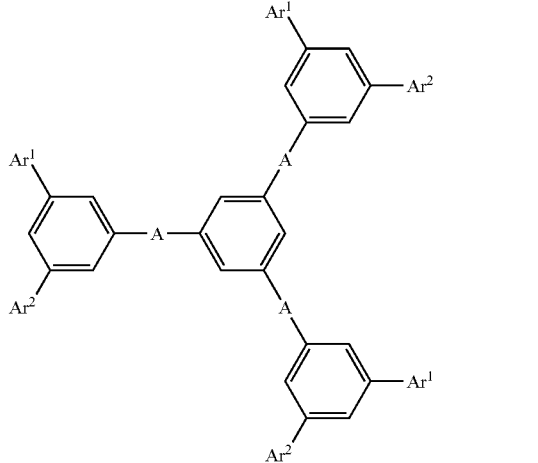
(b4)

Particular preference is given to the compounds wherein A denotes —S(O)$_2$—.

In the formulae (b2), (b3) and (b4), Ar$^1$, Ar$^2$ are defined as beforehand. Any hydrogen atom on a benzene ring may also be substituted with an alkyl group which preferably has 6 or less carbon atoms, a cycloalkyl group which is preferably a group having a 3- to 6-membered ring, an alkoxy group which preferably has 6 or less carbon atoms, a halogen which is preferably fluorine.

More specifically, particular preference is given to the compound denoted by the formula (b5) or (b6) below.

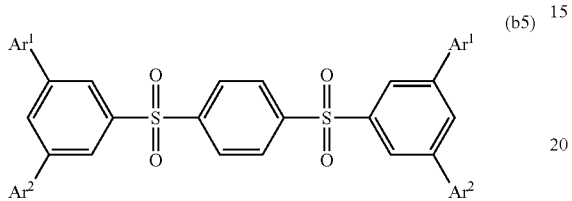

(b5)

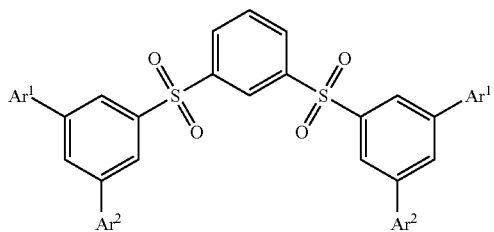

(b6)

in which, Ar$^1$ and Ar$^2$ preferably denote phenyl group.

The organosulfur compound of the present invention can be synthesized in accordance with the scheme 1 or scheme 2 described below.

Scheme 1:

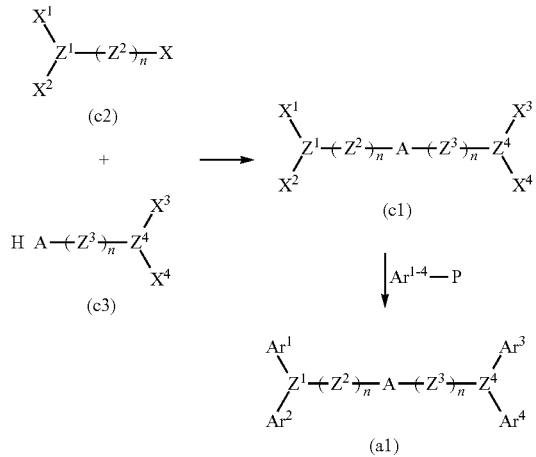

Scheme 2:

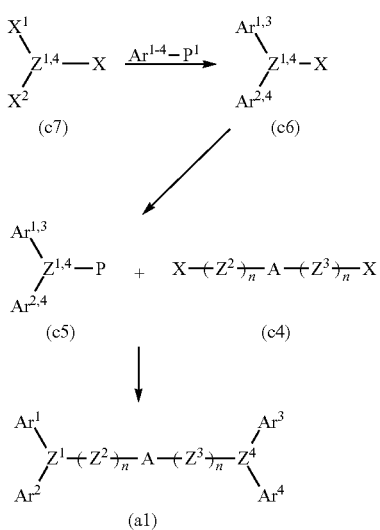

In the scheme 1 and scheme 2, A, Z$^1$ to Z$^4$, Ar$^1$ to Ar$^4$, and n are defined as in the formula (a1), X, X$^1$ to X$^4$ are selected from halogens, preferably Cl, Br and I, X is preferably Cl, Br and I, and X$^1$ to X$^4$ preferably denote Cl or Br, P and P$^1$ are an eliminative group which is selected so that a compound comprising P or P$^1$ is a boronic acid, a boronate ester, or an organometallic reagent.

Ar$^{1\ to\ 4}$ also denotes Ar$^1$ to Ar$^4$ collectively, Z$^{1,\ 4}$ in the formula (c7) denotes both Z$^1$ and Z$^4$, and in Ar$^{1,\ 3}$, Ar$^{2,\ 4}$ and Z$^{1,\ 4}$ in the formulae (c6) and (c5), the forward set and the backward set separated by "," denote compounds.

In the schemes described above, the reaction associated with the elimination of P or P$^1$ is preferably a catalytic coupling reaction (for example, the Suzuki coupling reaction, the Negishi coupling reaction and the like). Therefore, appropriate P or P$^1$ is selected in accordance with the coupling reaction.

When the compound comprising P or P$^1$ is a boronic acid or a boronate ester, P or P$^1$ is, for example, dihydroxyboryl group {—B(OH)$_2$}, or —B(OR$^1$)(OR$^2$) in which, R$^1$ and R$^2$ denote an alkyl group, or R$^1$ and R$^2$ denote together an alkylen group.

When the compound comprising P or P$^1$ is an organometallic reagent, the organometallic reagent includes the Grignard reagent, an organozinc reagent, an organotin reagent and an organolithium reagent. Therefore, P or P$^1$ denote, for example, the eliminative group in the Grignard reagent such as —MgCl, —MgBr, —MgI; the eliminative group in an organozinc reagent such as —ZnCl, —ZnBr, —ZnCl; the eliminative group in an organotin reagent such as —Sn(R$^1$)$_3$ in which, R$^1$ is defined in the same as the aforementioned; and, the eliminative group in an organolithium reagent such as —Li.

P and P$^1$ are preferably dihydroxyboryl group represented by {—B(OH)$_2$}, or —B(OR$^1$)(OR$^2$) wherein, R$^1$ and R$^2$ denote an alkyl group which are preferably a straight-chain or branched alkyl group having 12 or less carbon atoms. Alternatively, R$^1$ and R$^2$ may form together an alkylen group, preferably an alkylen group having 12 or less carbon atoms, which may be branched. It includes, for example, 4,4,5,5-tetramethyl-2,3-dioxaboryl group.

The production process of the present invention relates to a process for synthesizing the organosulfur compound denoted by the general formula (a1) by reacting the compound denoted by the general formula (c1) described above with the compound denoted by $Ar^{1\ to\ 4}$—P.

The different production process of the present invention furthermore relates to a process for synthesizing the general formula (a1) by reacting the compound denoted by the general formula (c4) described above with the compound denoted by the general formula (c5) described above.

When the scheme 1 and scheme 2 described above are applied to the synthesis of the compound of the general formula (a2), the summarization is denoted by the following scheme 3.

Scheme 3:

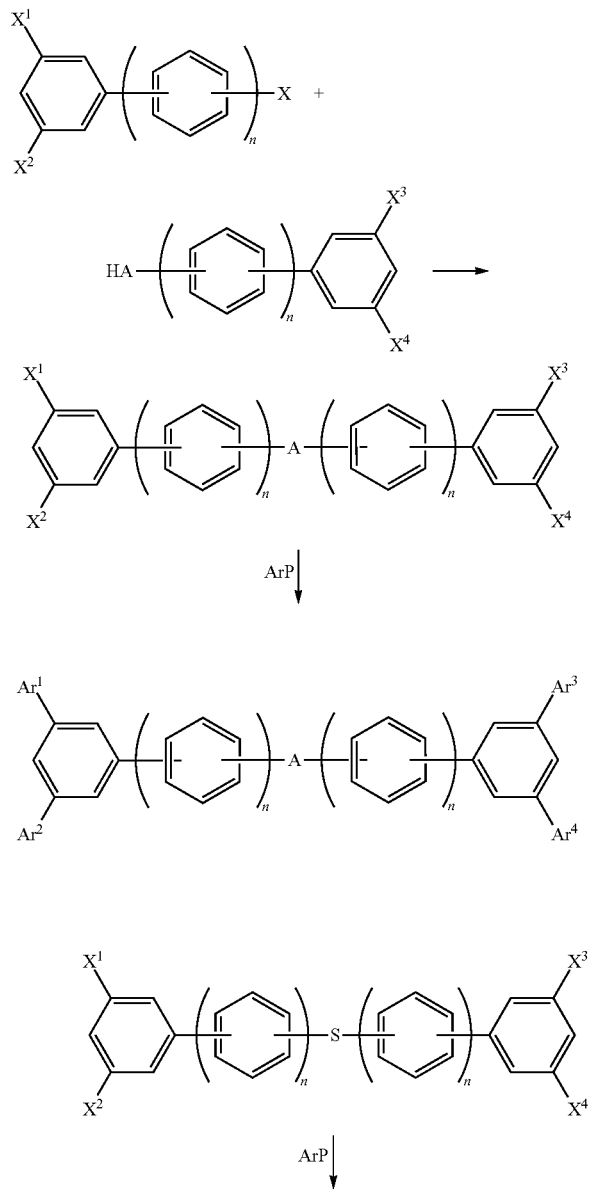

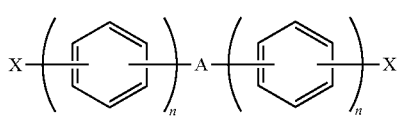

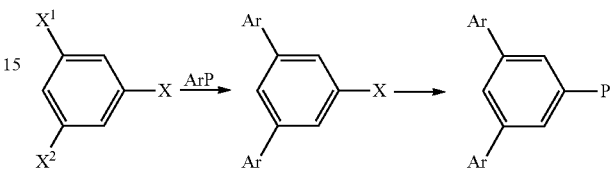

In the formula, A, $Ar^1$, $Ar^2$, $Ar^3$, $Ar^4$ and n are defined in the same as the aforementioned, and Ar is any one of $Ar^1$, $Ar^2$, $Ar^3$, $Ar^4$. P, X denote the meaning defined for the schemes 1 and 2, and each of P and X may be the same or different. Any hydrogen atom appearing on a benzene ring may be substituted with an alkyl group, a cycloalkyl group or an alkoxy group.

When A is —S(O)— or —S(O)$_2$— in the schemes 1 to 3, a compound having —S(O)— or —S(O)$_2$— may be a starting material, or a compound having thiol group may be a starting material and thioether group (—S—) may be converted to sulfinyl group (—SO—) or sulfonyl group (—S(O)$_2$—) by using an appropriate oxidant in the middle of production.

Taking the scheme 1 for instance, the following three processes may be possible in the event of synthesizing a compound wherein, for example, A is —S(O)$_2$— in the formula (a1).

(i) A compound is selected in which A is —S(O)$_2$— in the formula (c3) of the starting material;

(ii) The compound of the formula (c1) (A=-S—) is synthesized by selecting a compound in which A is —S— in the formula (c3) of the starting material, and at this step, the compound of the formula (c1) (A=-S(O)$_2$—) is synthesized by converting —S— to —S(O)$_2$—, and then the formula (a1) (A=-S(O)$_2$—) is synthesized in accordance with the pathway; or (iii) The compound of the formula (c1) (A=-S—) is synthesized by selecting a compound in which A is —S— in the formula (c3) of the starting material, and then the compound of the formula (a1) (A=-S—) is synthesized, and at this step the compound of the formula (a1) (A=-S(O)$_2$—) is synthesized by converting —S— to —S(O)$_2$—.

The example of the compound denoted by the formula (a2) is shown as follows.

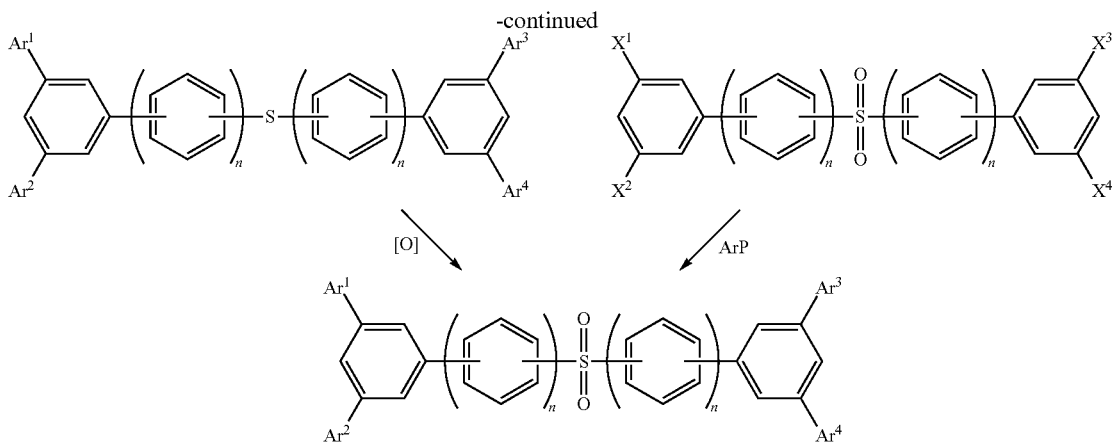

As the process for oxidizing thioether group (—S—), an oxidation process is adopted using, for example, oxygen, hydrogen peroxide (optionally an aqueous solution), an organic peroxide such as a ketone peroxide, m-chloroperoxybenzoic acid, Oxone® (the mixed salt consisting of potassium ion and hydrogen persulfate ion, sulfate ion and hydrogen sulfate ion).

The compound denoted by the general formula (b1) may be also synthesized in a manner analogous to the scheme 1 or scheme 2. One example is shown in the following scheme 4.

Scheme 4:

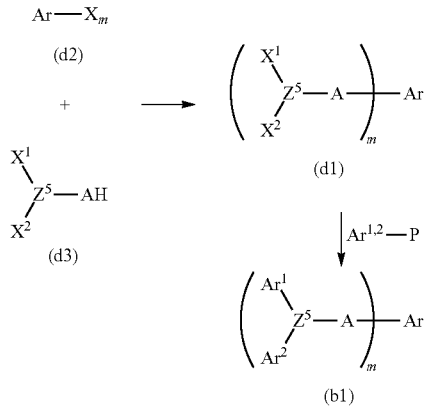

In the scheme 4, A, $Z^5$, Ar, $Ar^1$, $Ar^2$, and m are defined as in the formula (b1), X, $X^1$, $X^2$ are selected from halogens, preferably Cl, Br and I wherein m of X may be the same or different one another, X is preferably Br or I, and $X^1$ and $X^2$ are preferably Cl or Br, more preferably Cl.

P is an eliminative group which is selected so that a compound comprising P is a boronic acid, a boronate ester, or an organometallic reagent. The compound comprising P and the reaction associated with the elimination of P are explained as for the schemes 1 and 2.

One aspect of the production processes of the present invention relates to a process for synthesizing the organosulfur compound denoted by the general formula (b1) by reacting the compound denoted by the general formula (d1) described above with the compound denoted by $Ar^1$—P.

When A is —S(O)— or —S(O)$_2$— in the scheme 4, a compound having —S(O)— or —S(O)$_2$— may be a starting material, or a compound having thiol group may be a starting material and thioether group (—S—) may be converted to sulfinyl group (—SO—) or sulfonyl group (—S(O)$_2$—) by using an appropriate oxidant in the middle of production.

Taking the scheme 4 for instance, the following three processes may be possible in the event of synthesizing a compound wherein, for example, A is —S(O)$_2$— in the formula (b1).

(i) A compound is selected in which A is —S(O)$_2$— in the formula (d3) of the starting material;

(ii) The compound of the formula (d1) (A=-S—) is synthesized by selecting a compound in which A is —S— in the formula (d3) of the starting material, and at this step the compound of the formula (d1) (A=-S(O)$_2$—) is synthesized by converting —S— to —S(O)$_2$—, and then the formula (b1) (A=-S(O)$_2$—) is synthesized in accordance with the pathway; or (iii) The compound of the formula (d1) (A=-S—) is synthesized by selecting a compound in which A is —S— in the formula (d3) of the starting material, and then the compound of the formula (b1) (A=-S—) is synthesized, and at this step the compound of the formula (b1) (A=-S(O)$_2$—) is synthesized by converting —S— to —S(O)$_2$—.

The process for oxidizing thioether group aforementioned may be adopted.

Organic Electroluminescence Element

Next, the organic electroluminescence element of the present invention is explained. For the organic EL element of the present invention, known materials may be used except that the organosulfur compound of the present invention is used in a predetermined layer.

The organic EL element is preferably an organic EL element having a monolayer or multilayer of organic compound layer(s) between one pair of electrodes, and at least one layer of the organic compound layer(s) comprise(s) the compound of the present invention. The organic compound layer is a buffer layer, a hole injecting layer, a hole transporting layer, a emissive layer, a hole blocking layer, an electron transporting layer.

A monolayer-type organic EL element has an emissive layer between an anode and a cathode. An emissive layer contains an emissive material, and it may further contain a material used in an organic compound layer(s) by which holes injected from the anode or electrons injected from the cathode is transported to the emissive material, for example, a hole transporting material and a electron transporting material.

A multilayer-type organic EL element includes, for example, multilayer structures such as (anode/buffer layer/hole transporting layer/emissive layer/hole blocking layer/electron transporting layer/cathode) and (anode/buffer layer/hole transporting layer/emissive layer/electron transporting layer/cathode), and as well as including other multilayer structures such as (anode/hole injecting layer/hole transporting layer/emissive layer/hole blocking layer/electron transporting layer/metal oxide layer/cathode), (anode/hole injecting layer/emissive layer/cathode), (anode/emissive layer/electron transporting layer/cathode), (anode/hole injecting layer/emissive layer/electron transporting layer/cathode), and the structures thereof are not limited to these.

A buffer layer, a hole transporting layer, an electron transporting layer, and an emissive layer each may also have a monolayer structure or a multilayer structure. A layer having injection functionality (i.e. a hole injecting layer and an electron injecting layer) and a layer having transportation functionality (i.e. a hole transporting layer and an electron transporting layer) may also be equipped separately for each layer of a hole transporting layer, an electron transporting layer.

In terms of the constituent elements of the organic EL element of the present invention, the element constituent of (anode/buffer layer/hole transporting layer/emissive layer/hole blocking layer/electron transporting layer/cathode) is hereafter explained in detail for instance.

while the compound of the present invention may be contained within any layer, it is preferred to be contained within an emissive layer, a hole blocking layer and an electron transporting layer.

Any may be selected and used from known emissive materials for the material (hereafter, referred to as an emissive material) used in an emissive layer of organic layers in the organic EL element of the present invention. For example, it includes, without limitation to these, fluorescent materials such as anthracene, naphthalene, pyrene, tetracene, coronene, perylene, phthaloperylene, naphthaloperylene, diphenylbutadiene, tetraphenylbutadiene, coumarin, oxadiazole, bisbenzoxazorine, bisstyryl, cyclopentadiene, quinoline metal complex, tris(8-hydroxyquinolinate)aluminum complex, tris(4-methyl-8-quinolinate)aluminum complex, tris(5-phenyl-8-quinolinate)aluminum complex, aminoquinoline metal complex, benzoquinoline metal complex, tri-(p-terphenyl-4-yl)amine, 1-aryl-2,5-di(2-thienyl)pyrrole derivative, pyran, quinacridone, rubrene, distyrylbenzene derivative, distyrylarylene derivative, and phosphorescence emissive materials such as 4-acetylphenylethynyl[1,3-bis(2,6-diisopropylphenyl)imidazole-2-ylidene]gold, [2-(4,6-difluorophenyl)pyridinate-N,C2']iridium(III)picolinate (FIrpic), tris{1-[4-(trifluoromethyl)phenyl]-1H-pyrazolate,N,C2'}iridium(III) (Irtfmppz$_3$), bis[2-(4',6'-difluorophenyl)pyridinato-N,C2'] borate (Fir6), tris(2-phenylpyridinato)iridium(III).

An emissive layer may be formed from the aforesaid emissive material and a host material. It is necessary to use a host material especially when a phosphorescence material is used for an emissive layer. The known host materials include, without limitation to these, for example, 4,4'-di(N-carbazolyl)-1,1'-biphenyl (CBP), 1,4-di(N-carbazolyl)benzene, 2,2'-di[4"-(N-carbazolyl)phenyl]-1,1'-biphenyl (4CzPBP), diphenyldi(o-tolyl)silane, p-bis(triphenylsilyl)benzene, 9,10-bis-[1,1,3',1"']terphenyl-5'-yl-anthracene.

When an emissive material is used in combination with a host material, the emissive material is preferably in 0.005 to 40% by weight against the host material.

As a host material in an emissive layer, the organosulfur compound of the present invention may be used solely or in combination with other host materials.

The materials (hereafter, referred to as hole blocking materials) used as a hole blocking layer include, without limitation to these, for example, 2,9-dimethyl-4,7-diphenyl-1,10-phenanthroline, bis(2-methyl-8-quinolinolate)(p-phenylphenolate)aluminum, bis(2-methyl-8-quinolinolate)(triphenylsilanolate)aluminum and the like, as known materials.

As a hole blocking material, the organosulfur compound of the present invention may be used solely or in combination with other hole blocking materials.

The materials (hereafter, referred to as electron transporting materials) used as a electron transporting layer include, as known materials, for example, fluorene, phenanthroline, bathophenanthroline, bathocuproin, anthraquinodimethane, diphenoquinone, oxazole, oxadiazole, triazole, imidazole, anthraquinodimethane, 4,4'-N,N'-dicarbazolebiphenyl (CBP) and the like, their compounds, metal complex compounds or nitrogen-containing 5-membered ring derivatives. The metal complex compounds specifically include, without limitation to these, 8-hydroxyquinolinate lithium, tris(8-hydroxyquinolinate)aluminum, tri(2-methyl-8-hydroxyquinolinate)aluminum, tris(8-hydroxyquinolinate)gallium, bis(10-hydroxybenzo[h]quinolinate)beryllium, bis(10-hydroxybenzo[h]quinolinate)zinc, bis(2-methyl-8-quinolinate)(o-cresolate)gallium, bis(2-methyl-8-quinolinate)(1-naphtholate)aluminum, bis(2-methyl-8-quinolinate)-4-phenylphenolate and the like. As the aforesaid nitrogen-containing 5-membered ring derivatives, are also preferred oxazole, thiazole, oxadiazole, thiadiazole or triazole derivatives. There are specifically, without limitation to these, 2,5-bis(1-phenyl)-1,3,4-oxazole, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenylthiadiazolyl)]benzene, 2,5-bis(1-naphthyl)-1,3,4-triazole, 3-(4-biphenylyl)-4-phenyl-5-(4-t-butylphenyl)-1,2,4-thiazole and the like. Furthermore, the polymer materials used for polymer organic emissive elements may also be used. For example, they are, without limitation to these, polyparaphenylene and derivatives thereof, fluorene and derivatives thereof and the like.

As an electron transporting material, the organosulfur compound of the present invention may be used solely or in combination with other electron transporting materials.

On the other hand, the materials (hereafter, referred to as hole transporting materials) used as a hole transporting layer may be selected and used from known materials. For example, they include, without limitation to these, aromatic diamine compounds such as N,N'-bis(3-methylphenyl)-(1,1'-biphenyl)-4,4'diamine (TPD) and 4,4'-bis[N-(naphthyl)-N-phenyl-amino]biphenyl (α-NPD); stilbene derivatives; pyrazoline derivatives; polymer materials such as polyarylalkane, 4,4',4"-tris(N-(3-methylphenyl)N-phenylamino)triphenylamine (m-MTDATA), 2,2',7,7'-tetrakis-(N,N-diphenylamino)-9,9'-spirobifluorene, and polyvinylcarbazole.

A buffer layer may also be equipped in an organic EL element to improve the injectivity of holes, and the material used for a buffer layer may be selected and used from known materials. More preferably that in which molybdenum oxide from 1 to 30% by weight is doped into the above-described hole transporting material are used; however, they are not limited to this.

As the electrically-conductive material used for an anode, those with a work function higher than around 4 eV, for example, carbon atom, aluminum, vanadium, iron, cobalt, nickel, tungsten, silver, gold, platinum, palladium and alloys thereof, the ITO (the substance in which tin oxide from 5 to 10% was added into indium oxide) substrate, metal oxides such as tin oxide, indium oxide used for the NESA substrate, and further organic electrically-conductive resins such as polythiophene and polypyrrole may be used. In addition, it is preferred to use the electrically-conductive material used for an anode in the present element whose work function is higher than that used for a cathode by 0.1 eV or more.

As the electrically-conductive material used for a cathode, those with a work function lower than around 4 eV, for example, magnesium, calcium, tin, lead, titanium, yttrium, lithium, ruthenium, manganese, aluminum and the like or alloys thereof are used. The alloys include magnesium/silver, magnesium/indium, lithium/aluminum and the like. The ratio of an alloy is controlled by temperature of vapor deposition source, atmosphere, degree of vacuum and the like, and it is not particularly limited. In addition, it is preferred to use the electrically-conductive material used for a cathode in the present element whose work function is lower than that used for an anode by 0.1 eV or more.

In the organic EL element of the present invention, a metal oxide layer may also be equipped between an emissive layer and an electrode to improve the injectivity of electrons. A metal oxide may also be doped and used into an electron transporting material.

As a metal oxide to be used, an alkali metal fluoride such as LiF; an alkaline-earth metal fluoride such as $BaF_2$, $SrF_2$; an alkali metal oxide such as $Li_2O$; an alkaline-earth metal oxide such as RaO, SrO is used.

An anode and a cathode may be formed in a layer constitution with 2 or more layers if necessary.

In terms of the organic EL element of the present invention, it is desired for at least one side to be transparent in a luminescence wavelength range. It is also desired for a substrate to be transparent.

A transparent electrode is obtained by using the aforesaid electrically-conductive material and in setting so as to ensure a predetermined translucency through a process such as vapor deposition or sputtering.

An electrode on a luminescence side is desired for a light transmission rate to be 10% or higher.

While a substrate is not particularly limited as long as it has a mechanical, thermal strength and it has a transparency, a glass substrate or a transparent resin film is used.

The transparent resin film includes, for example, polyethylene, ethylene-vinyl acetate copolymer, ethylene-vinyl alcohol copolymer, polypropylene, polystyrene, polymethyl-methacrylate, polyvinyl chloride, polyvinyl alcohol, polyvinyl butyral, nylon, polyetheretherketone, polysulfone, polyethersulfone, tetrafluoroethylene-perfluoroalkyl vinyl ether copolymer, polyvinyl fluoride, tetrafluoroethylene-ethylene copolymer, tetrafluoroethylene-hexafluoropropylene copolymer, polychlorotrifluoroethylene, polyvinylidene fluoride, polyester, polycarbonate, polyurethane, polyimide, polyether imide, polyimide, polypropylene and the like.

For the organic EL element of the present invention, a protecting layer may be equipped on the surface of an element, or the entire element may be protected with silicon oil, resin and the like so that a stability against temperature, humidity, atmosphere and the like is improved.

For the formation of each layer of the organic EL element, may also be applied either a dry process for film formation such as vacuum vapor deposition, sputtering, plasma, ion plating, or a wet process for film formation such as spin coating, dipping, flow coating. A film thickness is preferably, but not particularly limited to, 0.1 nm to 10 μm, still preferably 0.5 nm to 0.2 μm.

In case of the wet process for film formation, a thin film may be prepared by solving or dispersing the present material on each layer in a solvent such as ethanol, chloroform, tetrahydrofuran, dioxan. At this step, it is also possible for the aforesaid materials to coexist.

EXAMPLES

The present invention will be explained specifically by the following examples.

Example 1

Synthesis of bis(4-(m-terphenyl-5'-yl)phenyl)sulfone

The compound entitled was synthesized in accordance with the following scheme.

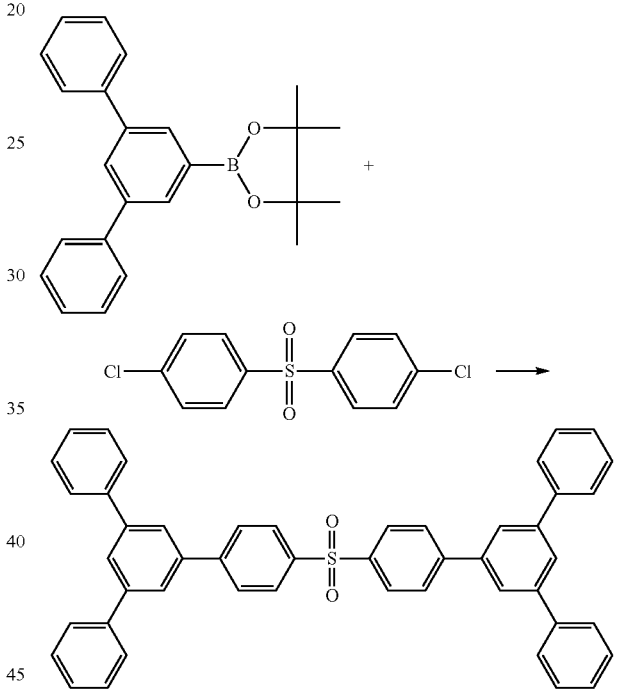

Into a 300 ml four-necked glass flask equipped with a thermometer, a reflux condenser and a stirrer, 2-(m-terphenyl-5'-yl)-4,4,5,5-tetramethyl-1,3,2-dioxaborane 11.3 g (31.7 mmol), bis(4-chlorophenyl)sulfone 3.50 g (12.2 mmol), 1.35 mol/l potassium phosphate aqueous solution 63.0 ml (85.1 mmol) and 1,4-dioxane 175 ml were added, and nitrogen was passed through the solution for 1 hour. Then, tris(dibenzylidene)acetone dipalladium(0) 270 mg (290 μmol) and tricyclohexylphosphine 210 mg (750 μmol) were added, which were reacted for 20 hours at 80 to 83° C. with stirring. After completion of the reaction, the reaction mixture was cooled down to room temperature and separated with the addition of water and ethyl acetate, and the organic layer obtained was dried with anhydrous magnesium sulfate. After filtration, the filtrate was concentrated under reduced pressure, and the obtained concentrate was purified in a sequence of silica-gel column chromatography (eluent; toluene), recrystallization (ethyl acetate), sublimation to obtain bis(4-(m-terphenyl-5'-yl)phenyl)sulfone 5.70 g as white solid (isolation yield; 69%).

Bis(4-(m-terphenyl-5'-yl)phenyl)sulfone is a novel compound, which is represented by the following property values.

EI-MS; 307, 674 (M)

$^1$H-NMR (CDCl$_3$, δ (ppm)); 7.34 to 7.56 (12H, m), 7.60 to 7.92 (18H, m), 8.04 to 8.14 (4H, m)

Example 2

Synthesis of bis(m-terphenyl-5'-yl)sulfone

The compound entitled was synthesized in accordance with the following scheme.

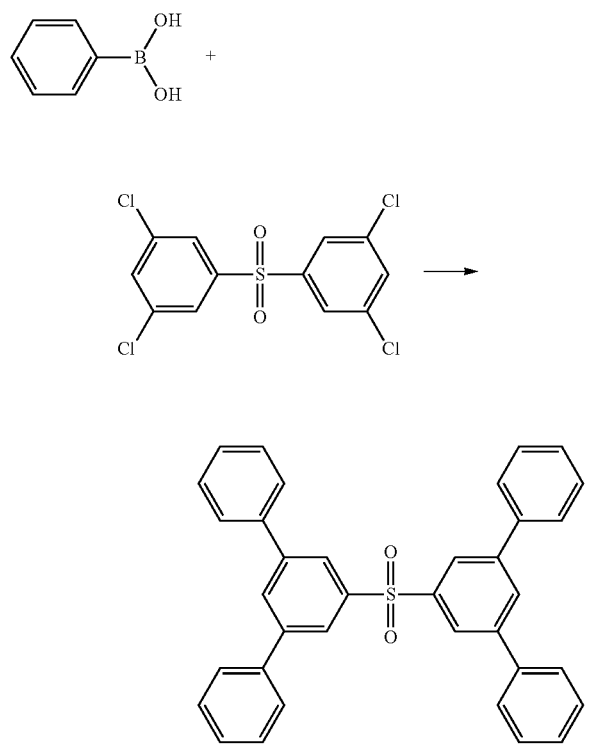

Into a 300 ml four-necked glass flask equipped with a thermometer, a reflux condenser and a stirrer, bis(3,5-dichlorophenyl)sulfone 1.50 g (4.20 mmol), phenylboronic acid 2.67 g (21.9 mmol), 1.35 mol/l potassium phosphate aqueous solution 21.8 ml (29.4 mmol) and 1,4-dioxane 125 ml were added, and nitrogen was passed through the solution for 1 hour. Then, tris(dibenzylidene)acetone dipalladium(0) 190 mg (210 μmol) and tricyclohexylphosphine 150 mg (530 μmol) were added, which were reacted for 24 hours at 80 to 83° C. with stirring. After completion of the reaction, the reaction mixture was cooled down to room temperature and precipitate solid was filtrated, which was washed with dioxane 50.0 ml, water 50.0 ml and methanol 50.0 ml and dried under vacuum. The obtained solid was purified by sublimation to obtain bis(m-terphenyl-5'-yl)sulfone 1.00 g as white solid (isolation yield; 45%).

Bis(m-terphenyl-5'-yl)sulfone is a novel compound, which was represented by the following property values.

EI-MS; 228, 522 (M)

$^1$H-NMR (CDCl$_3$, δ (ppm)); 7.36 to 7.53 (12H, m), 7.58 to 7.70 (8H, m), 7.93 to 8.00 (2H, m), 8.10 to 8.23 (4H, m)

Reference Example 1

Synthesis of 3,5-diphenylchlorobenzene

The compound entitled was synthesized in accordance with the following scheme.

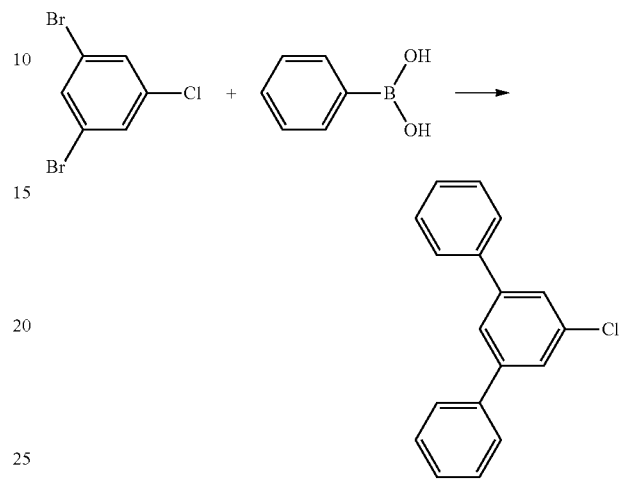

Into a 1 L four-necked glass flask equipped with a thermometer, a reflux condenser and a stirrer, 3,5-dibromochlorobenzene 20.0 g (74.0 mmol), phenylboronic acid 27.0 g (222 mmol), 2.0 mol/l sodium carbonate aqueous solution 285 ml (570 mmol), and toluene:tetrahydrofuran (1:1) solution 500 ml were added, and nitrogen was passed through the solution for 2 hours and 30 minutes. Tetrakistriphenylphosphine palladium(0) 4.28 g (3.70 mmol) was then added, which was reacted for 28 hours at 73 to 75° C. with stirring followed by further addition of phenylboronic acid 4.10 g (33.6 mmol) and tetrakistriphenylphosphine palladium(0) 1.10 g (950 μmol) and reaction for 24 hours at 73 to 75° C. with stirring. After completion of the reaction, the reaction mixture was cooled down to room temperature and separated with the addition of water and toluene, and after the water layer was extracted with toluene and after the organic layers were combined and washed with water, it was dried with anhydrous magnesium sulfate. After filtration, the filtrate was concentrated under reduced pressure, and the obtained concentrate was purified by silica-gel column chromatography (eluent: hexane) to obtain 3,5-diphenylchlorobenzene 16.0 g as white solid (isolation yield; 82%).

Reference Example 2

Synthesis of 2-(m-terphenyl-5'-yl)-4,4,5,5-tetramethyl-1,3,2-dioxaborane

The compound entitled was synthesized in accordance with the following scheme.

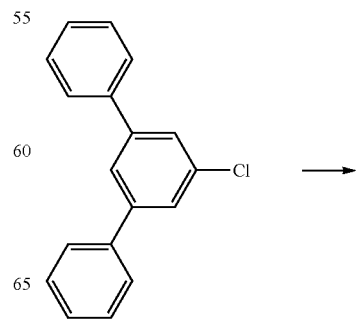

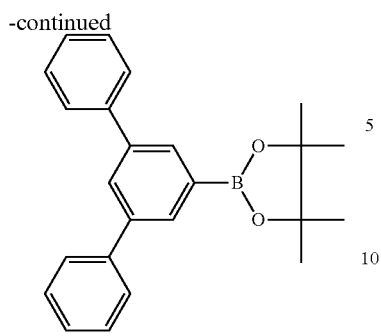

Into a 1 L four-necked glass flask equipped with a thermometer, a reflux condenser and a stirrer, 3,5-diphenylchlorobenzene 15.0 g (56.7 mmol) synthesized as the reference example 1, pinacolate diborane 20.2 g (79.5 mmol), potassium acetate 8.35 g (85.1 mmol) and dehydrated 1,4-dioxane 750 ml were added, and nitrogen was passed through the solution for 1 hour and 30 minutes. Then dibenzylideneacetone palladium(0) 1.96 g (3.41 mmol) and tricyclohexylphosphine 2.29 g (8.17 mmol) were added, which were reacted for 24 hours at 83 to 85° C. with stirring. After completion of the reaction, the reaction mixture was cooled down to room temperature and separated with the addition of saturated saline and ethyl acetate, and the organic layer obtained was dried with anhydrous magnesium sulfate. After filtration, the filtrate was concentrated under reduced pressure, and the obtained concentrate was purified by silica-gel column chromatography (eluents; hexane-chloroform) to obtain 2-(m-terphenyl-5'-yl)-4,4,5,5-tetramethyl-1,3,2-dioxaborane 15.6 g as white solid (isolation yield; 77%).

Reference Example 3

Synthesis of bis(3,5-dichlorophenyl)sulfide

The compound entitled was synthesized in accordance with the following scheme.

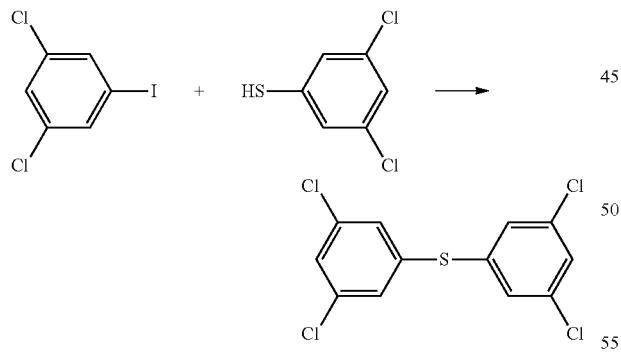

Into a 300 ml three-necked glass flask equipped with a thermometer, a reflux condenser and a stirrer, 3,5-dichloroiodobenzene 22.6 g (82.8 mmol) and dimethylformamide 200 ml were added, and argon was passed through the solution for 2 hours and 15 minutes. Then, 3,5-dichlorothiophenol 14.8 g (82.6 mmol), potassium carbonate 22.8 g (165 mmol) and cuprous iodide 1.57 g (8.24 mmol) were added, which were reacted for 3 hours at 95 to 100° C. with stirring. After completion of the reaction, the reaction mixture was cooled down to room temperature and separated with the addition of water and hexane:ethyl acetate (1:1), and the organic layer obtained was dried with anhydrous magnesium sulfate. After filtration, the filtrate was concentrated under reduced pressure, and the obtained concentrate was purified by recrystallization, simple silica-gel column chromatography (eluent; hexane) to obtain bis(3,5-dichlorophenyl)sulfide 25.4 g as white solid (isolation yield; 95%).

Reference Example 4

Synthesis of bis(3,5-dichlorophenyl)sulfone

The compound entitled was synthesized in accordance with the following scheme.

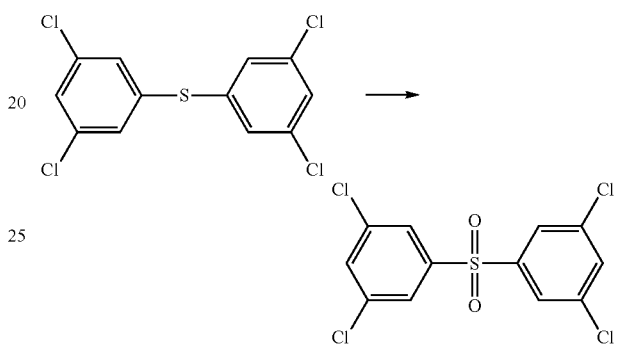

After methylene chloride 200 ml was added into a 1 L three-necked glass flask equipped with a thermometer, a calcium chloride tube and a stirrer and was cooled down to 0 to 5° C., 65% m-chloroperbenzoic acid 25.8 g (97.2 mmol) was added. Then, a solution, in which bis(3,5-dichlorophenyl)sulfide 14.3 g (44.1 mmol) synthesized as the reference example 3 was dissolved in methylene chloride 125 ml, was added dropwise with stirring and keeping at 0 to 10° C. After completion of adding dropwise, it was reacted overnight at room temperature. After completion of the reaction, the reaction mixture was washed with saturated sodium bicarbonate water, and the organic layer obtained was dried with anhydrous magnesium sulfate. After filtration, the filtrate was concentrated under reduced pressure, and the obtained concentrate was purified by column chromatography (eluents; hexane-toluene) to obtain bis(3,5-dichlorophenyl)sulfone 12.7 g as white solid (isolation yield; 81%). EI-MS; 354 (M), 356 (M+2), 358 (M+4)

Reference Example 5

Synthesis of 3,5-dichlorophenyl-3',5'-dibromophenylsulfide

The compound entitled was synthesized in accordance with the following scheme.

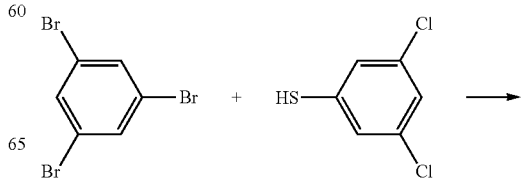

-continued

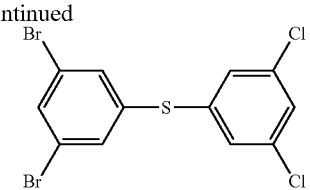

Into a 300 ml three-necked glass flask equipped with a thermometer, a reflux condenser and a stirrer, 1,3,5-tribromobenzene 43.9 g (140 mmol), potassium carbonate 28.9 g (210 mmol), cuprous iodide 2.65 g (14.0 mmol) and N,N-dimethylformamide 200 ml were added, and argon was passed through the solution. It was then reacted at 95 to 100° C. with adding 3,5-dichlorothiophenol 25.0 g (140 mmol), which was divided into each 5 g every one hour. After completion of the reaction, the reaction mixture was cooled down to room temperature and separated with the addition of water and hexane:ethyl acetate (1:1), and after the organic layer obtained was washed with saturated saline, it was dried with anhydrous magnesium sulfate. After filtration, the filtrate was concentrated under reduced pressure, and the obtained concentrate was purified by silica-gel column chromatography (eluent; hexane) to obtain 3,5-dichlorophenyl-3',5'-dibromophenylsulfide 20.0 g as white solid (isolation yield; 35%).

Reference Example 6

Synthesis of 3,5-dichlorophenyl-3',5'-dibromophenylsulfone

The compound entitled was synthesized in accordance with the following scheme.

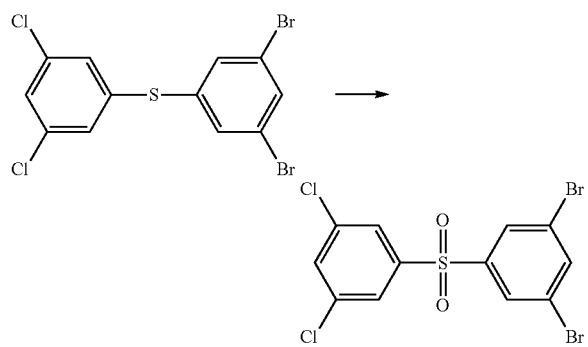

After methylene chloride 150 ml was added into a 500 ml four-necked glass flask equipped with a thermometer, a calcium chloride tube and a stirrer and was cooled down to 0 to 5° C., 65% m-chloroperbenzoic acid 21.2 g (79.9 mmol) was added. Then, a solution, in which 3,5-dichlorophenyl-3',5'-dibromophenylsulfide 15.0 g (36.3 mmol) synthesized as the reference example 5 was dissolved in methylene chloride 200 ml, was added dropwise with stirring and keeping at 0 to 10° C. After completion of adding dropwise, it was reacted overnight at room temperature. After completion of the reaction, the reaction mixture was washed with saturated sodium bicarbonate water, and the organic layer obtained was dried with anhydrous magnesium sulfate. After filtration, the filtrate was concentrated under reduced pressure, and the obtained concentrate was purified by column chromatography (eluent; hexane) to obtain 3,5-dichlorophenyl-3',5'-dibromophenylsulfone 10.0 g as white solid (isolation yield; 62%).

Example 3

Synthesis of bis(3,5-di-m-tolylphenyl)sulfone

The compound entitled was synthesized in accordance with the following scheme.

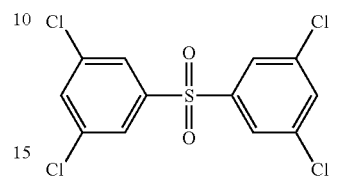

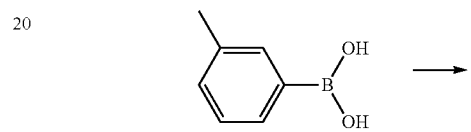

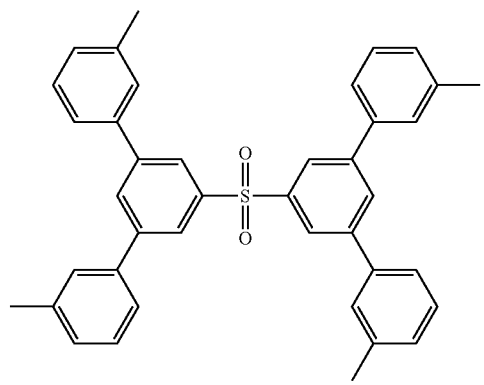

Into a 500 ml four-necked glass flask equipped with a thermometer, a reflux condenser and a stirrer, bis(3,5-dichlorophenyl)sulfone 2.50 g (7.00 mmol) synthesized as the reference example 4, 3-methylphenyl boronic acid 4.96 g (36.5 mmol), 1.35 mol/l potassium phosphate aqueous solution 36.4 ml (49.1 mmol) and 1,4-dioxane 225 ml were added, and nitrogen was passed through the solution for 1 hour. Then, tris(dibenzylidene)acetone dipalladium(0) 320 mg (350 μmol) and tricyclohexylphosphine 250 mg (890 μmol) were added, which were reacted for 20 hours at 80 to 83° C. with stirring. After completion of the reaction, the reaction mixture was cooled down to room temperature and an organic layer was separated. The organic layer obtained was concentrated under reduced pressure and the concentrate was purified by silica-gel chromatography (eluents; hexane-toluene) to obtain bis(3,5-di-m-tolylphenyl)sulfone 2.50 g as white solid (isolation yield; 60%).

Bis(3,5-di-m-tolylphenyl)sulfone is a novel compound, which was represented by the following property values.

EI-MS; 578 (M)

$^1$H-NMR (CDCl$_3$, δ (ppm)); 2.39 (12H, s), 7.12 to 7.50 (16H, m), 7.88 to 8.00 (2H, m), 8.08 to 8.20 (4H, m)

Example 4

Synthesis of bis(3,5-di-p-tolylphenyl)sulfone

The compound entitled was synthesized in accordance with the following scheme.

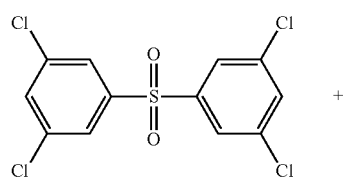

+

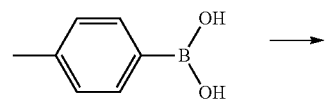

→

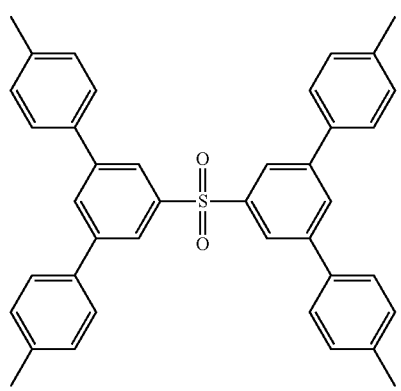

Into a 500 ml four-necked glass flask equipped with a thermometer, a reflux condenser and a stirrer, bis(3,5-dichlorophenyl)sulfone 2.50 g (7.00 mmol) synthesized as the reference example 4, 4-methylphenyl boronic acid 4.96 g (36.5 mmol), 1.35 mol/l potassium phosphate aqueous solution 36.4 ml (49.1 mmol) and 1,4-dioxane 225 ml were added, and nitrogen was passed through the solution for 1 hour. Then, tris(dibenzylidene)acetone dipalladium(0) 320 mg (350 μmol) and tricyclohexylphosphine 250 mg (890 μmol) were added, which were reacted for 20 hours at 80 to 83° C. with stirring. After completion of the reaction, the reaction mixture was cooled down to room temperature and precipitate solid was separated by filtration, which was washed with 1,4-dioxane, purified water and methanol and dried under vacuum. The obtained solid was purified by recrystallization (1,4-dioxane-methanol) to obtain bis(3,5-di-p-tolylphenyl)sulfone 3.30 g as white solid (isolation yield; 81%).

Bis(3,5-di-p-tolylphenyl)sulfone is a novel compound, which was represented by the following property values.

EI-MS; 578 (M)

$^1$H-NMR (CDCl$_3$, δ (ppm)); 2.39 (12H, s), 7.20 to 7.34 (8H, m), 7.46 to 7.58 (8H, m), 7.86 to 7.98 (2H, m), 8.08 to 8.20 (4H, m)

Example 5

Synthesis of bis(3,5-di-o-tolylphenyl)sulfone

The compound entitled was synthesized in accordance with the following scheme.

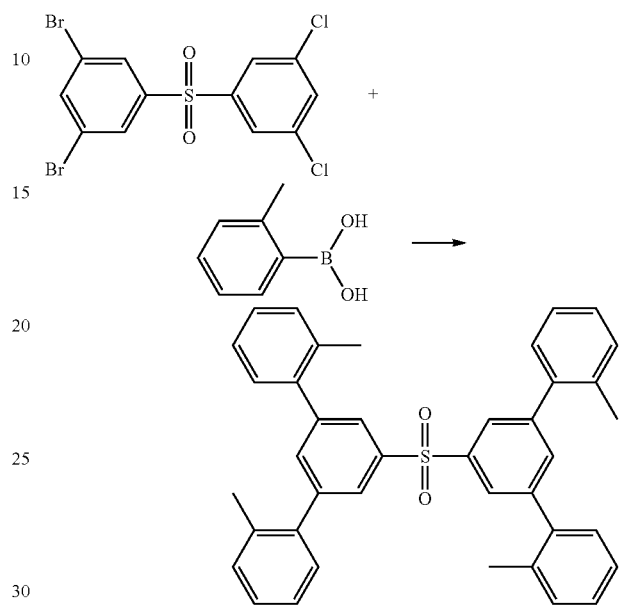

Into a 500 ml four-necked glass flask equipped with a thermometer, a reflux condenser and a stirrer, 3,5-dichlorophenyl-3',5'-dibromophenylsulfone 3.10 g (7.00 mmol) synthesized as the reference example 6, 2-methylphenyl boronic acid 4.96 g (36.5 mmol), 1.35 M potassium phosphate aqueous solution 36.4 ml (49.1 mmol) and 1,4-dioxane 225 ml were added, and nitrogen was passed through the solution for 1 hour. Then, tris(dibenzylidene)acetone dipalladium(0) 320 mg (350 μmol) and tricyclohexylphosphine 250 mg (890 μmol) were added, which were reacted for 25 hours at 80 to 83° C. with stirring. After completion of the reaction, the reaction mixture was cooled down to room temperature and was concentrated under reduced pressure. The obtained concentrate was purified by silica-gel chromatography (eluents: hexane-toluene) to obtain bis(3,5-di-o-tolylphenyl)sulfone 2.30 g as white solid (isolation yield; 57%).

Bis(3,5-di-o-tolylphenyl)sulfone is a novel compound, which was represented by the following property values.

EI-MS; 578 (M)

$^1$H-NMR (CDCl$_3$, δ (ppm)); 2.30 (12H, s), 7.20 to 7.38 (16H, m), 7.46 to 7.58 (2H, m), 7.85 to 7.98 (4H, m)

Example 6

Synthesis of bis(3,5-di-3-pyridylphenyl)sulfone

The compound entitled was synthesized in accordance with the following scheme.

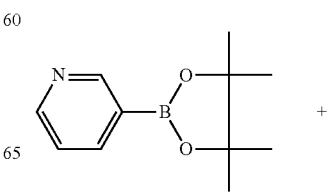

+

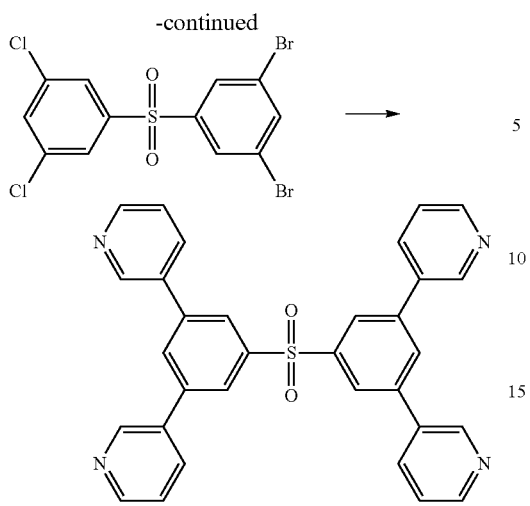

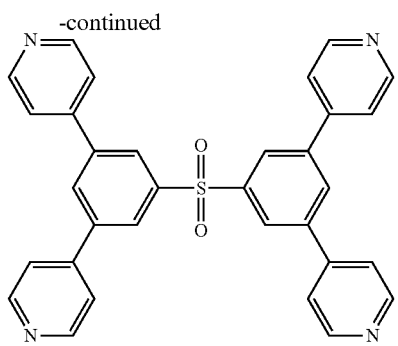

Into a 500 ml four-necked glass flask equipped with a thermometer, a reflux condenser and a stirrer, 3,5-dichlorophenyl-3',5'-dibromophenylsulfone 2.10 g (4.70 mmol) synthesized as the reference example 6, 2-(3-pyridyl)-4,4,5,5-tetramethyl-1,3,2-dioxaborane 5.00 g (24.4 mmol), 1.35 mol/l potassium phosphate aqueous solution 36.4 ml (49.1 mmol) and 1,4-dioxane 225 ml were added, and nitrogen was passed through the solution for 1 hour. Then, tris(dibenzylidene)acetone dipalladium(0) 210 mg (230 μmol) and tricyclohexylphosphine 160 mg (570 μmol) were added, which were reacted at 80 to 83° C. with stirring. After completion of the reaction, the reaction mixture was cooled down to room temperature and precipitate solid was separated by filtration, which was washed with 1,4-dioxane, purified water and methanol and dried under vacuum. The obtained solid was purified by silica-gel chromatography (eluents: chloroform-methanol) to obtain bis(3,5-di-3-pyridylphenyl)sulfone 800 mg as white solid (isolation yield; 32%).

Bis(3,5-di-3-pyridylphenyl)sulfone is a novel compound, which was represented by the following property values.

EI-MS; 526 (M)

$^1$H-NMR (CDCl$_3$, δ (ppm)); 7.32 to 7.50 (4H, m), 7.84 to 8.02 (6H, m), 8.14 to 8.28 (4H, m), 8.58 to 8.72 (4H, m), 8.76 to 8.92 (4H, m)

Example 7

Synthesis of bis(3,5-di-4-pyridylphenyl)sulfone

The compound entitled was synthesized in accordance with the following scheme.

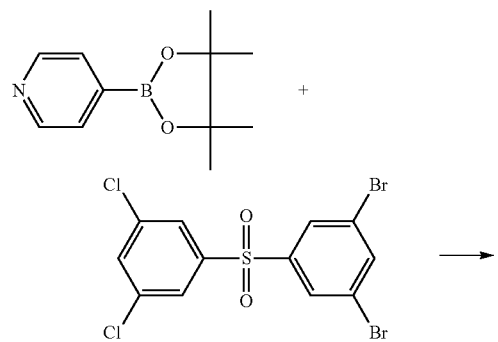

Into a 500 ml four-necked glass flask equipped with a thermometer, a reflux condenser and a stirrer, 3,5-dichlorophenyl-3',5'-dibromophenylsulfone 2.10 g (4.70 mmol) synthesized as the reference example 6, 2-(4-pyridyl)-4,4,5,5-tetramethyl-1,3,2-dioxaborane 5.00 g (24.4 mmol), 1.35 mol/l potassium phosphate aqueous solution 36.4 ml (49.1 mmol) and 1,4-dioxane 225 ml were added, and nitrogen was passed through the solution for 1 hour. Then, tris(dibenzylidene) dipalladium(0) 210 mg (230 μmol) and tricyclohexylphosphine 160 mg (570 μmol) were added, which were reacted at 80 to 83° C. with stirring. After completion of the reaction, the reaction mixture was cooled down to room temperature and precipitate solid was separated by filtration, which was washed with 1,4-dioxane, purified water and methanol and dried under vacuum. The obtained solid was purified by silica-gel chromatography (eluents: chloroform-methanol) to obtain bis(3,5-di-3-pyridylphenyl)sulfone 800 mg as white solid (isolation yield; 32%).

Bis(3,5-di-3-pyridylphenyl)sulfone is a novel compound, which was represented by the following property values.

EI-MS; 526 (M)

$^1$H-NMR (CDCl$_3$, δ (ppm)); 7.45 to 7.60 (8H, m), 8.00 to 8.10 (2H, m), 8.24 to 8.34 (4H, m), 8.66 to 8.82 (8H, m)

Reference Example 8

Synthesis of 1,3-bis(3',5'-dichlorophenylthio)benzene

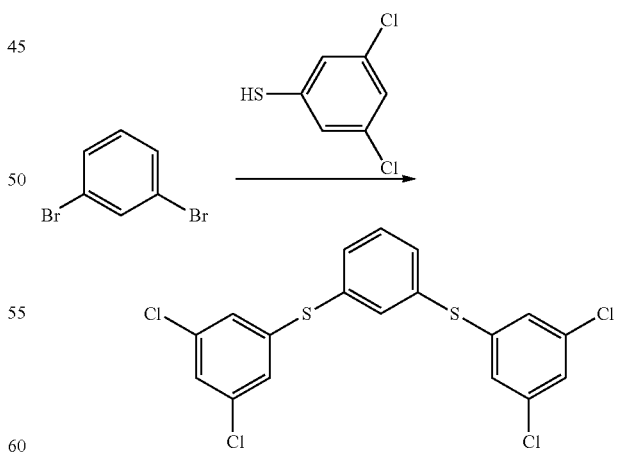

Into a 100 ml four-necked glass flask equipped with a stirrer, a thermometer and a reflux condenser, 1,3-dibromobenzene 2.36 g (10.0 mmol), potassium carbonate 5.52 g (40.0 mmol) and N,N-dimethylimidazolidinone 50.0 ml were added. Nitrogen was then passed through for 1 hour with stirring. Then cuprous iodide 3.76 g (21.0 mmol) and 3,5-dichlorobenzenethiol 3.76 g (21.0 mmol) were added, which were reacted for 24 hours at an inside temperature from 160 to 165° C. After completion of the reaction, they were separated with the addition of water and toluene, and after the organic layer obtained was dried with magnesium sulfate, it was filtrated and the obtained filtrate was concentrated under reduced pressure. The obtained concentrate was purified by silica-gel column chromatography (eluent: hexane) to obtain 1,3-bis(3',5'-dichlorophenylthio)benzene 2.36 g as white solid (isolation yield; 27%).

Reference Example 9

Synthesis of 1,4-bis(3',5'-dichlorophenylthio)benzene

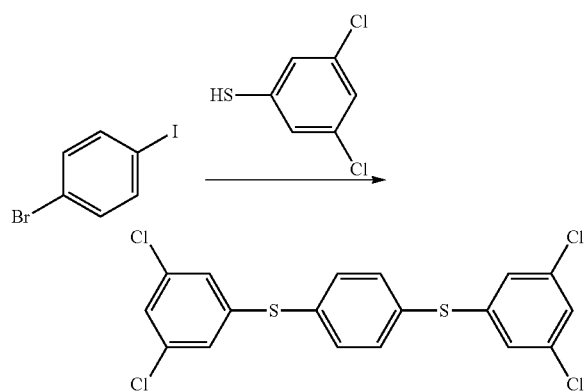

Into a 100 ml four-necked glass flask equipped with a stirrer, a thermometer and a reflux condenser, 4-bromoiodobenzene 2.83 g (10.0 mmol), potassium carbonate 5.52 g (40.0 mmol) and N,N-dimethylimidazolidinone 50.0 ml were added, and nitrogen was passed through for 1 hour with stirring. Then cuprous iodide 3.81 g (20.0 mmol) and 3,5-dichlorobenzenethiol 3.76 g (21.0 mmol) were added, which were reacted for 24 hours at an inside temperature from 160 to 165° C. After completion of the reaction, they were separated with the addition of water and toluene, and after the organic layer obtained was dried with magnesium sulfate, it was filtrated and the obtained filtrate was concentrated under reduced pressure. The obtained concentrate was purified by silica-gel column chromatography (eluent: hexane) to obtain 1,4-bis(3',5'-dichlorophenylthio)benzene 4.78 g as white solid (isolation yield; 55%).

Reference Example 10

Synthesis of 1,3-bis(3',5'-dichlorophenylsulfonyl)benzene

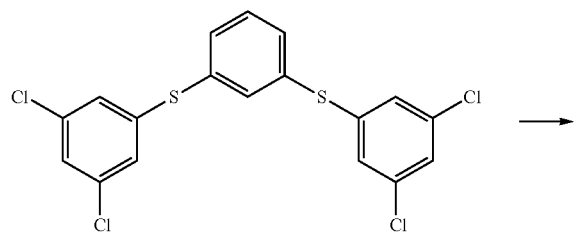

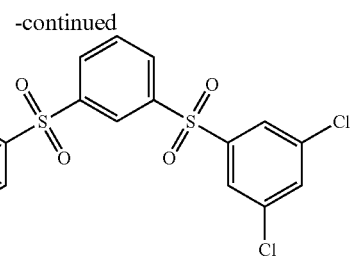

Methylene chloride 40.0 ml was added into a 100 ml four-necked glass flask equipped with a stirrer, a thermometer and a reflux condenser, and was cooled. After 65% by weight m-chloroperbenzoic acid 5.84 g (22.1 mmol) was then added, a solution, in which 1,3-bis(3',5'-dichlorophenylthio)benzene 2.36 g (5.49 mmol) synthesized as the reference example 8 was dissolved in methylene chloride 25 ml, was added dropwise so that an inside temperature was not higher than 10° C. After completion of adding dropwise and after stirring for 1 hour at 0 to 10° C., it was stirred overnight at room temperature. After completion of the reaction, it was separated with the addition of methylene chloride and saturated sodium bicarbonate water. After the organic layer obtained was washed with saturated sodium bicarbonate water, and after it was dried with magnesium sulfate, it was filtrated. The obtained filtrate was concentrated under reduced pressure and purified by silica-gel column chromatography (eluents; hexane/toluene=1/1 (volume ratio)) to obtain 1,3-bis(3',5'-dichlorophenylsulfonyl)benzene 2.40 g as white solid (isolation yield; 88%).

Example 8

Synthesis of 1,3-bis(3',5'-diphenylphenylsulfonyl)benzene

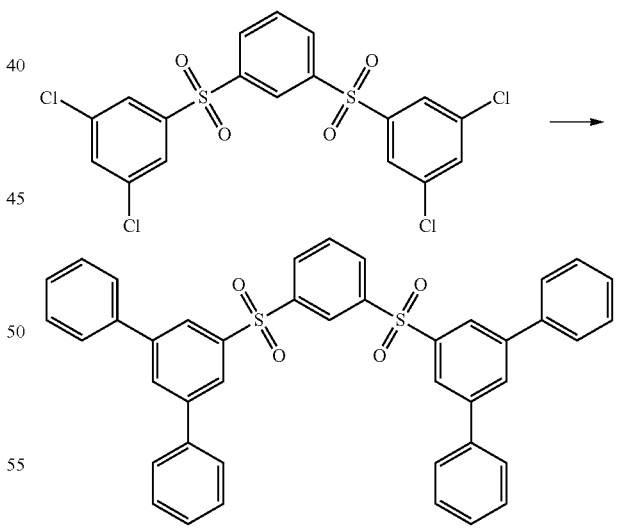

Into a 300 ml four-necked glass flask equipped with a stirrer, a thermometer and a reflux condenser, 1,3-bis(3',5'-dichlorophenylsulfonyl)benzene 2.40 g (4.85 mmol) synthesized as the reference example 10, phenylboronic acid 3.07 g (25.2 mmol), dioxane 340 ml and 1.35 mol/l potassium phosphate aqueous solution 25.2 ml (34.0 mmol) were added, and nitrogen was passed through for 1 hour with stirring. Then, trisdibenzylideneacetone palladium 220 mg (240 μmol) and tricyclohexylphosphine 170 mg (610 μmol) were added, which were reacted for 22 hours at an inside temperature from 80 to 85° C. After completion of the reaction, the reaction solution was concentrated under reduced pressure, and after the obtained concentrate was purified by silica-gel column chromatography (eluents: toluene/ethyl acetate=300/30 (volume ratio)), it was recrystallized with toluene-hexane (1:1). The obtained solid was then purified by silica-gel chromatography (eluent: chloroform) to obtain 1,3-bis(3',5'-diphenylphenylsulfonyl)benzene 1.70 g as white solid (isolation yield; 52%).

EI-MS (m/e); 662 (M)
$^1$H-NMR (CDCl$_3$, δ (ppm)); 8.64 (1H, s), 8.25 to 7.90 (8H, m), 7.75 to 7.20 (21H, m)

Reference Example 11

Synthesis of 1,4-bis(3',5'-dichlorophenylsulfonyl)benzene

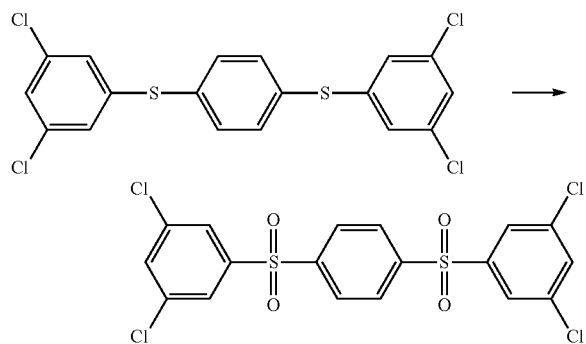

Methylene chloride 80.0 ml was added into a 300 ml four-necked glass flask equipped with a stirrer, a thermometer and a reflux condenser, and was cooled. After 65% by weight m-chloroperbenzoic acid 8.31 g (31.4 mmol) was then added, a solution, in which 1,4-bis(3',5'-dichlorophenyl)benzene 3.00 g (6.98 mmol) synthesized as the reference example 9 was dissolved in methylene chloride 30 ml, was added dropwise so that an inside temperature was not higher than 10° C. After completion of adding dropwise, and after stirring for 1 hour at 0 to 10° C., it was stirred overnight at room temperature. After completion of the reaction, it was separated with the addition of methylene chloride and saturated sodium bicarbonate water, and the organic layer and the aqueous layer were filtrated. After the obtained solids were washed with water, dioxane 250 ml was added and they were dissolved by heating. The obtained solution was cooled and precipitate solid was filtrated and collected to obtain 1,4-bis(3',5'-dichlorophenylsulfonyl)benzene 2.60 g as white solid (isolation yield; 75%).

Example 9

Synthesis of 1,4-bis(3',5'-diphenylphenylsulfonyl)benzene

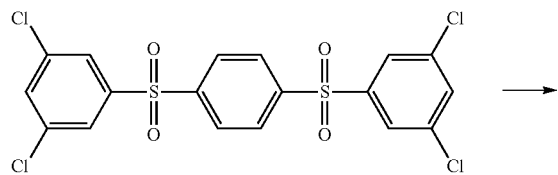

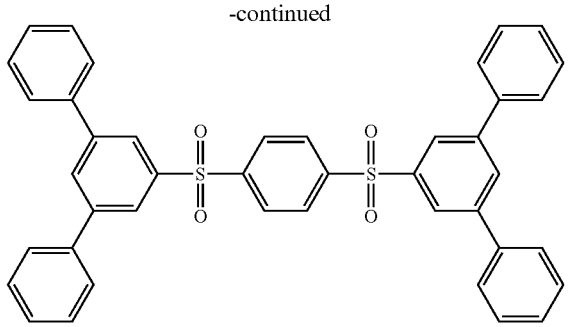

Into a 300 ml four-necked glass flask equipped with a stirrer, a thermometer and a reflux condenser, 1,4-bis(3',5'-dichlorophenylsulfonyl)benzene 2.55 g (5.16 mmol) synthesized as the reference example 11, phenylboronic acid 3.28 g (26.9 mmol), dioxane 260 ml and 1.35 mol/l potassium phosphate aqueous solution 34.0 ml (45.9 mmol) were added, and nitrogen was passed through for 1 hour with stirring. Then, trisdibenzylideneacetone dipalladium 240 mg (260 μmol) and tricyclohexylphosphine 190 mg (680 μmol) were added, which were reacted for 22 hours at an inside temperature from 80 to 85° C. Then trisdibenzylideneacetone dipalladium 480 mg (520 μmol) and tricyclohexylphosphine 380 mg (1.36 mmol) were appended and after completion of the reaction of reacting them for 40 hours at an inside temperature from 80 to 85° C., the reaction solution was concentrated under reduced pressure, and chloroform and water were added to the obtained concentrate, which was separated. After the obtained organic layer was dried with magnesium sulfate, it was filtrated and concentrated under reduced pressure. After the obtained concentrate was purified by silica-gel column chromatography (eluent: chloroform), 1,4-bis(3',5'-diphenylphenylsulfonyl)benzene 1.00 g was obtained as white solid (isolation yield; 29%).

EI-MS (m/e); 662 (M)
$^1$H-NMR (CDCl$_3$, δ (ppm)); 8.18 to 8.02 (8H, m), 8.00 to 7.95 (2H, m), 7.68 to 7.35 (20H, m)

Next, are explained the production examples of the organic EL element using the compound of the present invention.

Element Production Example 1

As shown in FIG. 1, an organic EL element was made by the following process, which was equipped with each layer of a transparent substrate 1, an anode 2, a buffer layer 3, a hole transporting layer 4, an emissive layer 5, a hole blocking layer 6, an electron transporting layer 7 and a cathode 8 from the side of the substrate.

In the production examples, the following abbreviations are used. BTPS: bis(m-terphenyl-5'-yl)sulfone; Those synthesized in the example 2 were used. BTPPS: bis(4-(m-terphenyl-5'-yl)phenyl)sulfone; Those synthesized in the example 1 were used.

A glass substrate (Transparent substrate 1) on which a transparent conductive film patterned (ITO) (Anode 2) was deposited with a film thickness of 110 nm was treated by cleaning in a sequence of ultrasonic cleaning with purified water and a surfactant, cleaning with running purified water, ultrasonic cleaning with a solution of 1:1 purified water and isopropyl alcohol, and cleaning with boiling isopropyl alcohol. This substrate was slowly lifted from boiling isopropyl alcohol and dried in vapor of isopropyl alcohol, and finally cleaned with ultraviolet and ozone. This substrate, as an anode, was placed in a vacuum chamber, which was evacuated until 1×10⁻⁶ Torr and in the chamber were installed respective molybdenum boards filled with each evaporation material and an evaporation mask for film formation with a predetermined pattern, and by applying electric current and heat on the boards to vaporize the evaporation materials, were sequentially deposited a buffer layer 3, a hole transporting layer 4, an emissive layer 5, a hole blocking layer 6, an electron transporting layer 7 as follows.

By co-evaporating NS21 (made by Nippon Steel Chemical Co., Ltd) of a hole transporting material and molybdenum trioxide ($MoO_3$) on the aforesaid substrate, NS21:$MoO_3$=80:20 was deposited into a film thickness of 10 nm, then, NS21:$MoO_3$=90:10 was deposited into a film thickness of 20 nm to form a buffer layer 3. NS21 was subsequently deposited into a film thickness of 5 nm to form a hole transporting layer 4. Then, NS21:EY52 (made by e-Ray Optoelectronics Technology Co., Ltd. (hereafter referred to as e-Ray Co.))=98.7:1.3 was deposited into a film thickness of 20 nm, and furthermore EB43 (made by e-Ray Co.):EB52 (made by e-Ray Co.) was deposited into a film thickness of 30 nm, so that an emissive layer 5 became a white element. Bis(2-methyl-8-quinolinolate)(p-phenylphenolate)aluminum (BAlq) was deposited on the emissive layer 5 into a film thickness of 5 nm to form a hole blocking layer 6.

On the hole blocking layer 6, BTPS was furthermore deposited into a film thickness of 17 nm, and BTPS:8-hydroxyquinolinate lithium (Liq)=74:26 was furthermore deposited into a film thickness of 10 nm to form an electron transporting layer 7. A film of aluminum (Al) was deposited thereon into a film thickness of 100 nm to form a cathode 8.

The layered structure formed in this way was combined with another glass substrate, which were encapsulated with a UV-curable resin to accomplish an element.

The layer structure of the present element is simplistically shown by,
Anode 2: ITO (110 nm),
Buffer layer 3: NS21:$MoO_3$ (10 nm, 80:20)/NS21:$MoO_3$=(20 nm, 90:10),
Emissive layer 5: NS21:EY52 (20 nm, 98.7:1.3)/EB43:EB52 (30 nm, 98.8:1.2),
Hole blocking layer 6: BAlq (5 nm),
Electron transporting layer 7: BTPS (17 nm)/BTPS:Liq (10 nm, 74:26),
Cathode 8: Al (100 nm).

Element Production Example 2

An element was made in a similar manner to the element production example 1 except that BAlq of the hole blocking layer was replaced with BTPS and 1,4-di(1,10-phenanthroline-2-yl)benzene (DPB) was used in place of BTPS used in the electron transporting layer in the element production 1.

The layer structure is,
Anode 2: ITO (110 nm),
Buffer layer 3: NS21:$MoO_3$ (10 nm, 80:20)/NS21:$MoO_3$=(20 nm, 90:10),
Hole transporting layer 4: NS21 (5 nm),
Emissive layer 5: NS21:EY52 (20 nm, 98.7:1.3)/EB43:EB52 (30 nm, 98.8:1.2),
Hole blocking layer 6: BTPS (5 nm),
Electron transporting layer 7: DPB (14 nm)/DPB:Liq (10 nm, 74:26),
Cathode 8: Al (100 nm).

Element Production Example 3

An element was made in a similar manner to the element production example 1 except that BTPPS was used in place of BTPS in the element production 1.

The layer structure of the present element is simplistically shown by,
Anode 2: ITO (110 nm),
Buffer layer 3: NS21:$MoO_3$ (10 nm, 80:20)/NS21:$MoO_3$=(20 nm, 90:10),
Hole transporting layer 4: NS21 (5 nm),
Emissive layer 5: NS21:EY52 (20 nm, 98.7:1.3)/EB43:EB52 (30 nm, 98.8:1.2),
Hole blocking layer 6: BAlq (5 nm),
Electron transporting layer 7: BTPPS (17 nm)/BTPPS:Liq (10 nm, 74:26),
Cathode 8: Al (100 nm).

Element Production Example 4

An element was made in a similar manner to the element production example 2 except that BTPS was replaced with BTPPS in the element production 2.

The layer structure of the present element is simplistically shown by,
Anode 2: ITO (110 nm),
Buffer layer 3: NS21:$MoO_3$ (10 nm, 80:20)/NS21:$MoO_3$=(20 nm, 90:10),
Hole transporting layer 4: NS21 (5 nm),
Emissive layer 5: NS21:EY52 (20 nm, 98.7:1.3)/EB43:EB52 (30 nm, 98.8:1.2),
Hole blocking layer 6: BTPPS (5 nm),
Electron transporting layer 7: DPB (14 nm)/DPB:Liq (10 nm, 74:26),
Cathode 8: Al (100 nm).

Element Production Example 5

Figure 2:
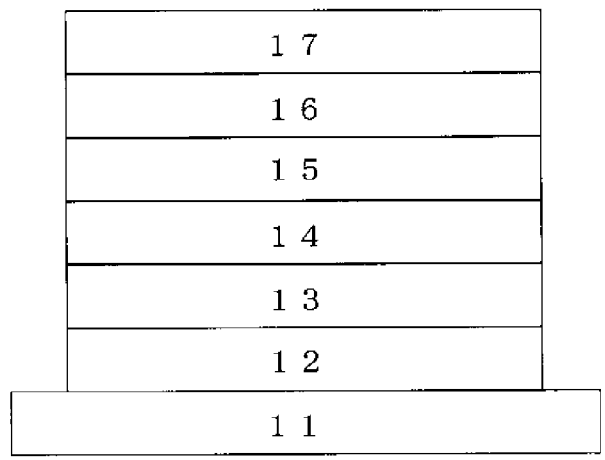
FIG. 2 shows the layer constitution of the organic EL element produced in the element production examples 5 to 7.

As shown in FIG. 2, an organic EL element was made in a similar manner to the element production example 1, which was equipped with each layer of a transparent substrate 11, an anode 12, a buffer layer 13, a hole transporting layer 14, an emissive layer 15, an electron transporting layer 16 and a cathode 17 from the side of the substrate.

The layer structure is as follows.
Anode 12: ITO (110 nm),
Buffer layer 13: NS21:$MoO_3$ (10 nm, 80:20)/NS21:$MoO_3$= (20 nm, 90:10),
Hole transporting layer 14: 3DTAPBP (20 nm),
Emissive layer 15: 4-acetylphenylethynyl[1,3-bis(2,6-diisopropylphenyl)imidazole-2-ylidene]gold:BTPS (10 nm, 80:20),
Electron transporting layer 16: BmPyPB (50 nm)/Liq (0.5 nm),
Cathode 17: Al (100 nm).

3DTAPBP, 4-acetylphenylethynyl[1,3-bis(2,6-diisopropylphenyl)imidazole-2-ylidene]gold, BmPyPB are the compounds denoted by the structural formulae described below, which are described in JP-A-2005-320277, WO2005-80515 and JP-A-2008-127326, respectively.

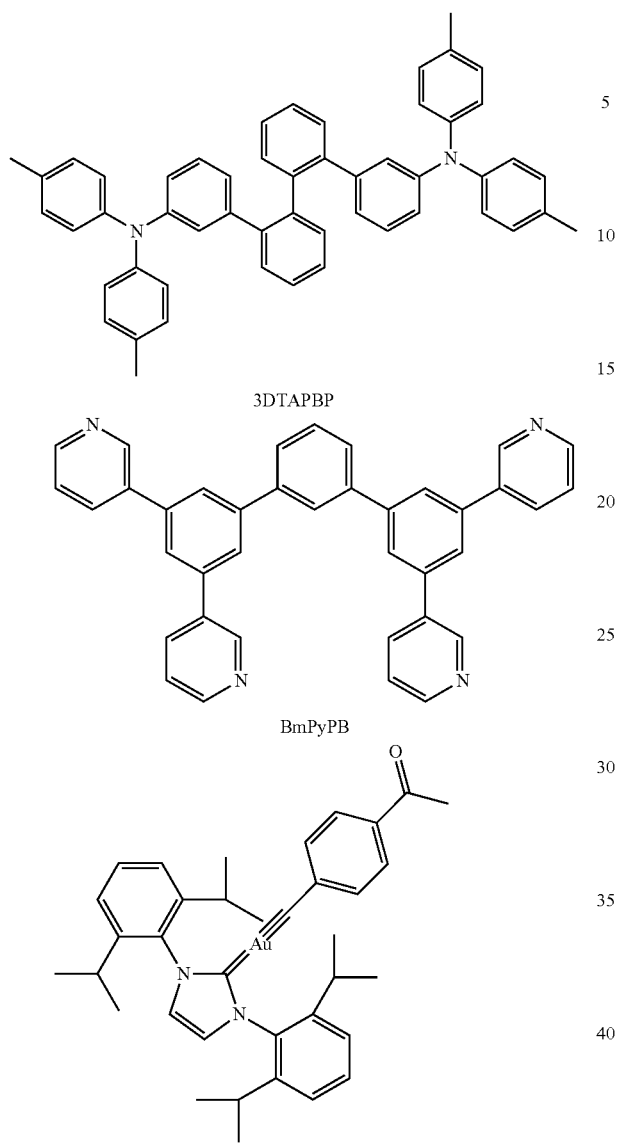

Element Production Example 6

An organic EL element was made in a similar manner to the element production example 1, which was equipped with each layer shown in FIG. 2.

The layer constitution is as follows.

Anode 12: ITO (110 nm),

Buffer layer 13: NS21:MoO₃ (20 nm, 80:20),

Hole transporting layer 14: 3DTAPBP (20 nm),

Emissive layer 15: FIrpic: BTPS (4.5 nm, 20:80)/PQ2Ir (dpm):BTPS (1.0 nm, 5:95)/FIrpic:BTPS (4.5 nm, 80:20), Electron transporting layer 16: BmPyPB (25 nm)/KLET03 (47 nm)/Liq (1.0 nm), Cathode 17: Al (100 nm).

FIrpic, PQ2Ir (dpm) are the dopant denoted by the structural formulae described below, and KLET03 is the electron transporting material made by Chemipro Kasei, Ltd.

Element Production Example 7

An element with the layer structure simplistically shown as described below was made in a similar manner to the element production example 6 except that BTPS was replaced with BTPPS.

The layer structure is as follows.

Anode 12: ITO (110 nm),

Buffer layer 13: NS21:MoO₃ (20 nm, 80:20),

Hole transporting layer 14: 3DTAPBP (20 nm),

Emissive layer 15: FIrpic:BTPPS (4.5 nm, 20:80)/PQ2Ir (dpm):BTPPS (1.0 nm, 5:95)/FIrpic: BTPPS (4.5 nm, 80:20), Electron transporting layer 16: BmPyPB (25 nm)/KLET03 (47 nm)/Liq (1.0 nm), Cathode 17: Al (100 nm).

The organic EL elements made in the element production examples 1 to 7 as described above were connected to a power source ("2400" made by KETHELEY Inc.), and the measurements of an external quantum efficiency, luminous efficiency, an energy conversion efficiency were carried out by means of a multichannel analyzer ("CS-2000" made by Konica Minolta Inc.). The results are shown in Table 1 and Table 2.

TABLE 1

Property evaluation results of each element

| | External quantum efficiency (%) | | | Luminous efficiency (lm/W) | | | Energy conversion efficiency (%) | | |
|---|---|---|---|---|---|---|---|---|---|
| | 10 A/m² | 100 A/m² | 1000 A/m² | 10 A/m² | 100 A/m² | 1000 A/m² | 10 A/m² | 100 A/m² | 1000 A/m² |
| Element production example 1 | 3.3 | 2.7 | 1.4 | 2.8 | 1.8 | 0.6 | 1.0 | 0.6 | 0.2 |
| Element production example 2 | 5.3 | 4.6 | 3.6 | 11.7 | 8.3 | 4.6 | 3.7 | 2.6 | 1.4 |

TABLE 1-continued

Property evaluation results of each element

| | External quantum efficiency (%) | | | Luminous efficiency (lm/W) | | | Energy conversion efficiency (%) | | |
|---|---|---|---|---|---|---|---|---|---|
| | 10 A/m² | 100 A/m² | 1000 A/m² | 10 A/m² | 100 A/m² | 1000 A/m² | 10 A/m² | 100 A/m² | 1000 A/m² |
| Element production example 3 | 2.1 | 2.2 | 1.8 | 2.4 | 1.9 | 1.1 | 1.1 | 0.8 | 0.5 |
| Element production example 4 | 3.2 | 2.9 | 2.2 | 3.8 | 2.5 | 1.4 | 2.0 | 1.4 | 0.8 |

TABLE 2

| | External quantum efficiency (%) | | | Luminous efficiency (lm/W) | | | Energy conversion efficiency (%) | | |
|---|---|---|---|---|---|---|---|---|---|
| | 1 A/m² | 2.5 A/m² | 25 A/m² | 1 A/m² | 2.5 A/m² | 25 A/m² | 1 A/m² | 2.5 A/m² | 25 A/m² |
| Element production example 5 | 2.31 | 1.58 | 0.32 | 5.96 | 3.53 | 0.45 | 1.75 | 1.07 | 0.15 |
| Element production example 6 | 18.2 | 17.6 | 13.8 | 42.3 | 39.3 | 24.6 | 14.1 | 13.1 | 8.3 |
| Element production example 7 | 6.4 | 5.9 | 4.9 | 15.9 | 14.0 | 10.0 | 5.3 | 4.7 | 3.3 |

INDUSTRIAL APPLICABILITY

The organosulfur compound of the present invention is useful as the material of an organic EL element.

EXPLANATION OF SIGNS

1. Transparent substrate
2. Anode
3. Buffer layer
4. Hole transporting layer
5. Emissive layer
6. Hole blocking layer
7. Electron transporting layer
8. Cathode
11. Transparent substrate
12. Anode
13. Buffer layer
14. Hole transporting layer
15. Emissive layer
16. Electron transporting layer
17. Cathode

The invention claimed is:

1. An organosulfur compound denoted by a general formula (a1):

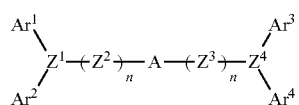

(a1)

in which,
A denotes —S(O)₂—,
Z¹ and Z⁴ denote

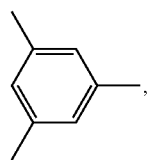

Z² and Z³ denote 1,4-phenylene,
Ar¹, Ar², Ar³ and Ar⁴ denote a phenyl group, tolyl group or pyridyl group, wherein Ar¹, Ar², Ar³ and Ar⁴ are all the same, and
n is 0 or 1, wherein two of n are the same, or,
a general formula (b1):

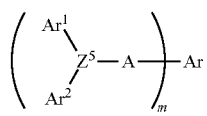

(b1)

in which,
A denotes —S(O)₂—,
Z⁵ denotes

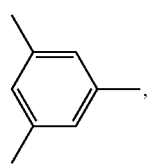

Ar denotes a divalent residue derived from benzene,
Ar¹ and Ar² denote a phenyl group, tolyl group or pyridyl group, wherein Ar¹ and Ar² are the same, and,
m is 2.

2. An organosulfur compound according to claim 1, denoted by a general formula (a5), (a6), (b5) or (b6):

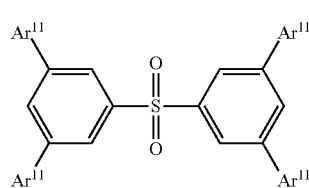

(a5)

-continued

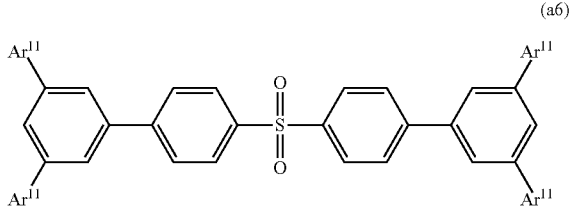
(a6)

in which, $Ar^{11}$ denotes a phenyl group, tolyl group or pyridyl group, and

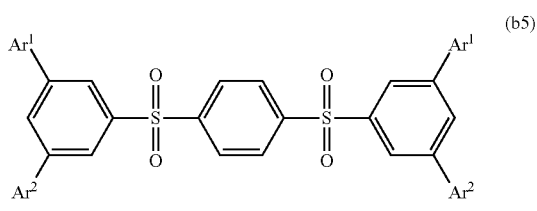
(b5)

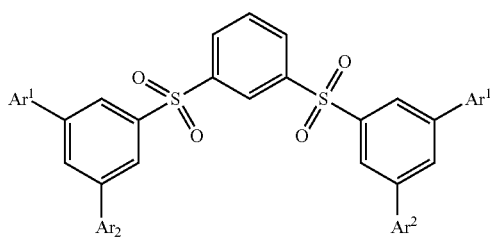
(b6)

in which, $Ar^1$ and $Ar^2$ denote a phenyl group.

3. A process for producing a compound denoted by a general formula (a1):

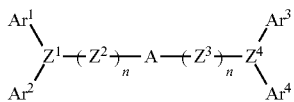
(a1)

in which,

A denotes $—S(O)_2—$, $Z^1$ and $Z^4$ denote

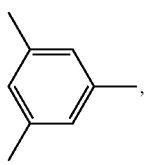, $Z^2$ and $Z^3$ denote 1,4-phenylene, $Ar^1$, $Ar^2$, $Ar^3$ and $Ar^4$ denote a phenyl group, tolyl group or pyridyl group, wherein $Ar^1$, $Ar^2$, $Ar^3$ and $Ar^4$ are all the same, and n is 0 or 1, wherein two of n are the same;

wherein a compound denoted by a general formula (c1):

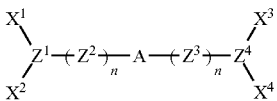
(c1)

in which,

A, $Z^1$, $Z^4$, $Z^2$, $Z^3$ and n denote the meanings as defined for said general formula (a1), $X^1$, $X^2$, $X^3$ and $X^4$ independently denote a halogen, is reacted with a compound denoted by formulae:

$Ar^1P$, $Ar^2P$, $Ar^3P$ and $Ar^4P$ in which, $Ar^1$, $Ar^2$, $Ar^3$ and $Ar^4$ denote the meanings as defined for said general formula (a1); P is an eliminative group which is selected so that a compound comprising P is a boronic acid, a boronate ester, or an organometallic reagent.

4. A process for producing a compound denoted by a general formula (a1):

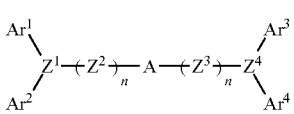
(a1)

in which,

A denotes $—S(O)_2—$, $Z^1$ and $Z^4$ denote

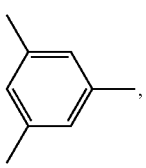, $Z^2$ and $Z^3$ denote 1,4-phenylene, $Ar^1$, $Ar^2$, $Ar^3$ and $Ar^4$ denote a phenyl group, tolyl group or pyridyl group, wherein $Ar^1$, $Ar^2$, $Ar^3$ and $Ar^4$ are all are the same, and n is 0 or 1, wherein two of n are the same;

wherein a compound denoted by a general formula (c4):

(c4)

in which,

A, $Z^2$, $Z^3$ and n denote the meanings as defined for said general formula (a1), and X denotes a halogen, and two of X may be the same or different, is reacted with a compound denoted by general formulae (c5i) and (c5ii):

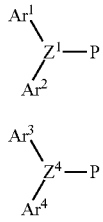 (c5i)

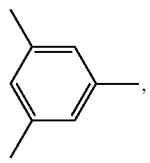 (c5ii)

in which,
Ar$^1$, Ar$^2$, Ar$^3$, Ar$^4$, Z$^1$ and Z$^4$ denote the meanings as defined in said general formula (a1),
P is an eliminative group which is selected so that a compound comprising P is a boronic acid, a boronate ester, or an organometallic reagent.

5. A process for producing a compound denoted by a general formula (b1):

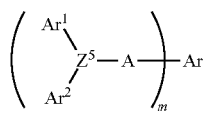 (b1)

in which,
A denotes —S(O)$_2$—,
Z$^5$ denotes

Ar denotes a divalent residue derived from benzene,
Ar$^1$ and Ar$^2$ denote a phenyl group, tolyl group or pyridyl group, wherein Ar$^1$ and Ar$^2$ are the same, and
m is 2,
wherein a compound denoted by a general formula (d1):

$$\left( \begin{array}{c} X^1 \\ Z^5-A \\ X^2 \end{array} \right)_m Ar \quad (d1)$$

in which,
A, Ar, Z$^5$ and m denote the meanings as defined for said general formulae (b1),
X$^1$ and X$^2$ independently denote a halogen,
is reacted with a compound denoted by formulae Ar$^1$P and Ar$^2$P in which, Ar$^1$ and Ar$^2$ denote the meanings as defined in said general formula (b1); P is an eliminative group which is selected so that a compound comprising P is a boronic acid, a boronate ester, or an organometallic reagent.

6. An organic electroluminescence element comprising the organosulfur compound according to claim 1.

7. An organic electroluminescence element according to claim 6, wherein at least one layer selected from an electron transporting layer, a hole blocking layer and an emissive layer comprises the organosulfur compound according to claim 1.

8. An organic electroluminescence element according to claim 7, wherein the emissive layer comprises 4-acetylphenylethynyl[1,3-bis(2,6-diisopropylphenyl)imidazole-2-ylidene]gold.

* * * * *